United States Patent
Alix-Panabieres et al.

(10) Patent No.: US 11,525,826 B2
(45) Date of Patent: Dec. 13, 2022

(54) METHOD FOR DETECTING AND/OR CHARACTERISING TUMOUR CELLS AND ASSOCIATED APPARATUS

(71) Applicants: CHU MONTPELLIER, Montpellier (FR); ECOLE SUPERIEURE DE PHYSIQUE ET DE CHIMIE INDUSTRIELLES DE LA VILLE DE PARIS, Paris (FR); Centre national de la recherche scientifique, Paris (FR); Université de Montpellier, Montpellier (FR); AxLR, SATT du Languedoc Roussillon, Montpellier (FR)

(72) Inventors: Catherine Michèle Marilou Alix-Panabieres, Clapiers (FR); Andrew David Griffiths, Paris (FR); Raphaël Clément Li-Ming Doineau, Paris (FR); Clément Nizak, Paris (FR); Philippe Chi-Thanh Nghe, Saint-Mande (FR); Jean-Marie Pierre Baudry, Paris (FR); Elodie Michèle Christine Brient-Litzler, Versailles (FR); Klaus Eyer, Paris (FR); Jérôme Bibette, Paris (FR)

(73) Assignees: Chu Montpellier, Montpellier (FR); Ecole Superieure De Physique Et De Chimie Industrielles De La Ville De Paris, Paris (FR); Centre National De La Recherche Scientifique, Paris (FR); Université De Montpellier, Montpellier (FR); Axlr, Satt Du Languedoc Roussillon, Montpellier (FR)

( * ) Notice: Subject to any disclaimer, the term of this patent is extended or adjusted under 35 U.S.C. 154(b) by 912 days.

(21) Appl. No.: 16/093,934

(22) PCT Filed: Apr. 18, 2017

(86) PCT No.: PCT/EP2017/059209
§ 371 (c)(1),
(2) Date: Feb. 11, 2019

(87) PCT Pub. No.: WO2017/178662
PCT Pub. Date: Oct. 19, 2017

(65) Prior Publication Data
US 2019/0170741 A1 Jun. 6, 2019

(30) Foreign Application Priority Data
Apr. 15, 2016 (FR) .................................... 1653383

(51) Int. Cl.
*G01N 33/543* (2006.01)
*B01L 3/00* (2006.01)
(Continued)

(52) U.S. Cl.
CPC .. *G01N 33/54333* (2013.01); *B01L 3/502784* (2013.01); *G01N 33/532* (2013.01);
(Continued)

(58) Field of Classification Search
CPC .......... G01N 33/54333; G01N 33/532; G01N 33/5436; G01N 33/57496; B01L 3/502784; B01L 2200/0673
See application file for complete search history.

(56) References Cited

U.S. PATENT DOCUMENTS

| 8,415,173 B2 * | 4/2013 | Harriman | G01N 33/5436 436/535 |
| 9,534,246 B2 * | 1/2017 | Kotsopoulou | G01N 33/566 |

(Continued)

OTHER PUBLICATIONS

Deng et al. An Integrated Microfluidic Chip System for Single-Cell Secretion Profiling of Rare Circulating Tumor Cells. Scientific Reports 4: 7499. pp. 1-8 (Dec. 16, 2014).*
(Continued)

*Primary Examiner* — Gailene Gabel
(74) *Attorney, Agent, or Firm* — B. Aaron Schulman, Esq.; Stites & Harbison, PLLC

(57) ABSTRACT

The present invention relates to the field of biological diagnosis in oncology. It relates to a method and apparatus for detecting and/or characterizing tumor cells by detecting one or more elements of the tumor cell secretome, in particular one or more peptides or proteins, and, in particu-
(Continued)

Figure 1:
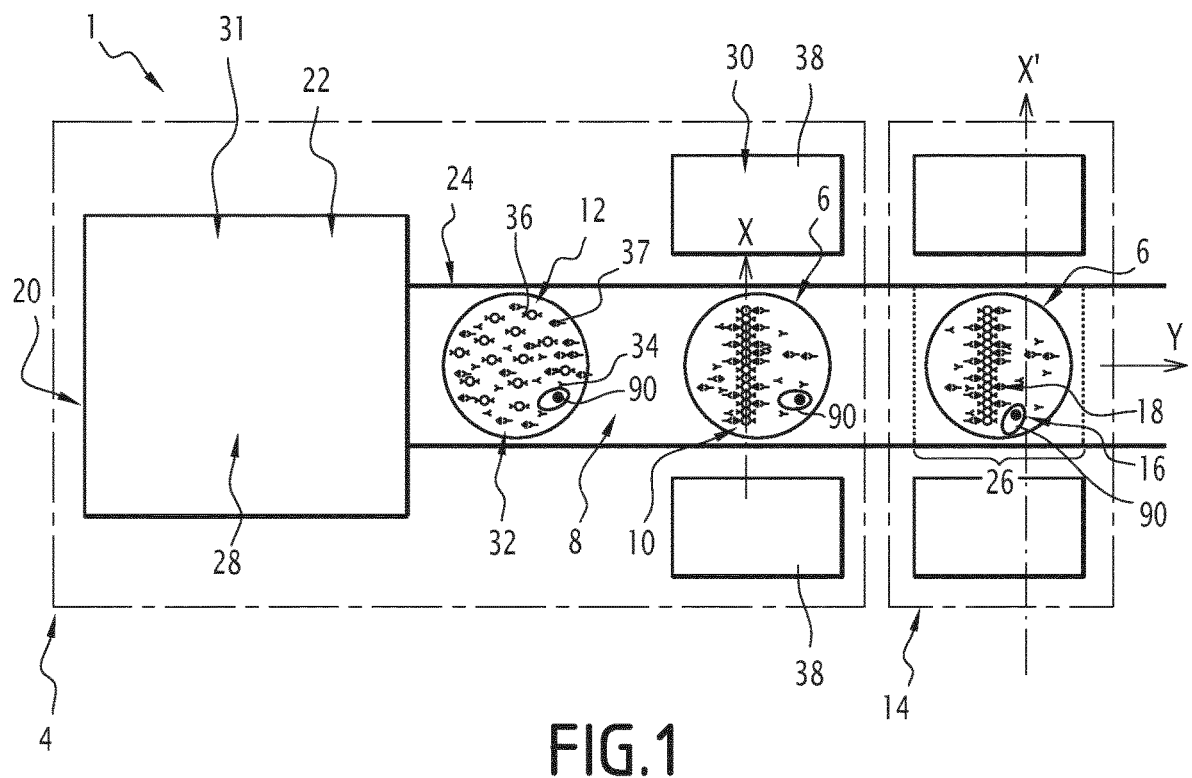

lar, one or more tumor markers. The invention also relates to detecting and/or characterizing droplets of tumor cells and their method of preparation.

9 Claims, 14 Drawing Sheets

(51) Int. Cl.
G01N 33/532 (2006.01)
G01N 33/574 (2006.01)
(52) U.S. Cl.
CPC ... G01N 33/5436 (2013.01); G01N 33/57496 (2013.01); *B01L 2200/0673* (2013.01)

(56) References Cited

U.S. PATENT DOCUMENTS

| 9,562,897 | B2 | 2/2017 | Samuels et al. |
| 9,575,061 | B2 | 2/2017 | Haselton et al. |
| 9,981,230 | B2 | 5/2018 | Link et al. |
| 10,416,168 | B2* | 9/2019 | Griffiths ............... G01N 33/543 |
| 2005/0079557 | A1 | 4/2005 | Vendrell et al. |
| 2006/0078893 | A1 | 4/2006 | Griffiths et al. |
| 2007/0077572 | A1 | 4/2007 | Tawfik et al. |
| 2008/0176289 | A1* | 7/2008 | Zeng ..................... G06T 7/11 435/91.2 |
| 2012/0015382 | A1* | 1/2012 | Weitz .................. B01F 13/0076 435/7.92 |
| 2014/0342373 | A1* | 11/2014 | Viovy ............... B01L 3/502784 435/7.4 |
| 2017/0028365 | A1 | 2/2017 | Link et al. |
| 2017/0307626 | A1 | 10/2017 | Griffiths et al. |

OTHER PUBLICATIONS

Preliminary Search Report dated Dec. 19, 2016.
Bruno Teste et al, "11A low cost and high throughput magnetic bead-based immuno-agglutination assay in confined droplets 11", Lab on a Chip, vol. 13, No. 12, Mar. 26, 2013 (Mar. 26, 2013), pp. 2344-2349, XP055202306, ISSN: 1473-0197, DOI: 10.1039/03lc50353d the whole document.
Ryan Tewhey et al: 11 Microdroplet-based PCR enrichment for large-scale targeted sequencing 11, Nature Biotechnology, vol. 27, No. 11, Nov. 1, 2009 (Nov. 1, 2009), pp. 1025-1031, XP055103848, ISSN: 1087-0156, DOI: 10.1038/nbt.1583 the whole document.
Mazutis et al: Single-cell analysis and sorting using droplet-based microfluidics, Nature Protocols, vol. 8, No. 5, pp. 870-891, Apr. 4, 2013.
Alix-Panabieres, et al.: Challenges in circulating tumour cell research, Nature Reviews/Cancer, vol. 14, pp. 623-631, Sep. 2014.
Griffiths, et al, "Directed evolution of an extremely fast phosphotriesterase by in vitro compartmentalization", 2003, pp. 24-35, vol. 22, No. 1, the EMBO Journal.

* cited by examiner

METHOD FOR DETECTING AND/OR CHARACTERISING TUMOUR CELLS AND ASSOCIATED APPARATUS

FIELD OF THE INVENTION

The present invention relates to the field of biological diagnosis in oncology. It relates to a method and apparatus for detecting and/or characterizing tumor cells by detecting one or more secretome elements of the tumor cell, in particular one or more peptides or proteins, and in particular one or more tumor markers. The invention also relates to detection and/or characterization droplets of tumor cells and their method of preparation.

BACKGROUND OF THE INVENTION

The article "*Challenges in circulating tumor cell research*" in the publication Nature Reviews Cancer published in September 2014, volume 14, p. 623 to 6131, describes various technologies for detecting circulating tumor cells.

A method for detecting circulating tumor cells commonly designated by the acronym EPISPOT (Epithelial Immunospot) is known from the prior art, in particular from EP 1 506 407. This technique allows the detection of circulating tumor cells in a biological sample of a patient with solid cancer, by detecting tumor markers released by these cells. It involves the deposition of cells on a solid culture surface, more particularly 96-well plates, at a rate of $2.10^5$ cells per well, wherein a specific antibody for a tumor marker of interest is fixed on this solid culture surface, followed by culturing these cells, then washing the cells out, and detecting the tumor marker of interest with a specific marked antibody.

However, the resolution obtained by such a method is limited. In fact, the detected proteins come from different cells in the same well. It is difficult to know which cell secreted what. The signal does not provide information on cell heterogeneity. In addition, it is difficult to recover cells in order to analyze their genotype.

The present invention aims to provide a more accurate and reliable detection method.

WO 2009/011808 A1 describes a method for determining an activity for fixing a protein within a droplet.

The "*Single-cell analysis and sorting using droplet-based microfluidics*" published online by Mazutis et al., on 4 Apr. 2013 in the publication Nature Protocols, illustrates this principle.

A mouse hybridoma is encapsulated in a droplet with a bead coated with anti-mouse antibodies. The hybridoma secretes antibodies. A secondary antibody coupled to a fluorophore makes it possible to reveal the presence of the secreted antibody. The distribution of the secondary antibody is homogeneous in the droplet in the absence of secreted antibodies, but it relocates on the bead in the presence of antibodies. This method is therefore very selective in determining the activity of a particular cell.

On the other hand, such a method has various disadvantages. The method of compartmentalization of cells and beads is random. The number of beads in the droplets may be estimated by a Poisson distribution law. Similarly, the number of cells within the droplets may be estimated by an independent Poisson distribution law. Initial concentrations of beads and droplets are adjusted to average one cell and one bead per droplet. Only a portion of the droplets is, therefore, of interest for the analysis performed.

Moreover, the presence of a single bead of significant size per droplet is not favorable to the implementation of the method. In fact, the secondary antibodies are distributed over the entire surface of the bead. The dynamic range of the method is therefore limited by the available external surface per bead.

BRIEF SUMMARY OF THE INVENTION

An object of the invention is to provide a more reliable and more sensitive method of analysis than existing methods, thus allowing the analysis of the secretome of living cells, either singly or in the form of an aggregate, for detecting and/or characterizing cells. tumors, and, in particular, single tumor cells or aggregates of tumor cells.

For this purpose, the object of the invention is a method for detecting and/or characterizing tumor cells, comprising:
supplying a plurality of droplets contained in a carrier fluid, wherein at least one of the droplets comprises at least one aggregate of particles defining an object elongated along a main axis, wherein at least some droplets contain a cell capable of producing at least one target secretome element of a tumor cell capable of being fixed to the aggregate;
measuring at least one physical parameter that is characteristic of the fixing of a target secretome element of a tumor cell on the aggregate; and
the detection and/or characterization of tumor cells from the measurement of the at least one physical parameter.

More specifically, the method for detecting and/or characterizing tumor cells according to the invention comprises:
providing a plurality of droplets contained in a carrier fluid, wherein the droplets comprise a plurality of particles capable of forming an aggregate of particles defining an object elongated along a main axis, wherein at least some droplets contain a cell;
incubating the plurality of droplets under conditions and for a sufficient time so that, in the droplets containing a cell, the cell is capable of producing at least one target secretome element of a tumor cell that is capable of being fixed on the aggregate;
formation in each droplet of at least one aggregate of particles defining an object elongated along a main axis;
measuring at least one physical parameter, wherein each physical parameter is characteristic of the fixing of a target element distinct from the secretome of a tumor cell on the aggregate; and
detection and/or characterization of tumor cells from the measurement of the at least one physical parameter.

DETAILED DESCRIPTION OF EXEMPLARY EMBODIMENTS

The cell is a single cell or an aggregate of cells, in particular, an aggregate suspected to be an aggregate of tumor cells.

The aggregates of tumor cells are of oligoclonal origin and result from the adhesion, or grouping, of several primary tumor cells. Aggregates of tumor cells may typically contain 2 to 15 tumor cells. They consist essentially of tumor cells, but may also contain other types of cells, such as leukocytes, platelets, in limited numbers.

The method according to the invention therefore relates, in particular, to a method for detecting and/or characterizing single tumor cells comprising:

providing a plurality of droplets contained in a carrier fluid, wherein at least one of the droplets comprises at least one aggregate of particles defining an object elongated along a main axis, wherein at least some droplets contain a single cell;

incubating the droplets containing a single cell under conditions and for a sufficient time for the single cell to be capable of producing at least one target secretome element of a tumor cell that is capable of being fixed on the aggregate;

measuring at least one physical parameter, wherein each physical parameter is characteristic of the fixing of a target element distinct from the secretome of a tumor cell on the aggregate; and detection and/or characterization of single tumor cells from the measurement of the at least one physical parameter.

By "single-cell droplet" is meant that the droplet comprises a single cell.

By "single tumor cell-containing droplet" is meant that the droplet comprises a single cell that is a tumor cell.

Within the context of the invention, a tumor cell is not a cell created by artificial fusion of a tumor cell with another cell, such as a hybridoma.

In particular, the method is intended to determine the presence of droplets, or even to select droplets, comprising a single cell whose secretome comprises a particular target element, wherein this target element is a molecule of the secretome of a tumor cell, and, in particular, a tumor marker.

The secretome of a cell is the set of elements (organic or inorganic molecules, such as proteins, peptides, carbohydrates, lipids, or nucleic acids, or vesicles) present in the conditioned medium of a cell in culture. The term "secretome" refers in a particular sense to the portion of the proteome (i.e. all of the proteins and peptides expressed by the cell) that is present in the conditioned medium of a cell in culture.

These molecules, and, in particular, proteins or peptides are:

secreted (by the so-called 'classical' pathway involving the endoplasmic reticulum and the Golgi apparatus, or by so-called 'non-classical' pathways such as active transport through a membrane transporter protein, or secretion via recycling endosomes or vacuoles of exocytosis). This is the case, for example, of the protein Prostate Specific Antigen (PSA), mammaglobin, human kallikrein 3 (hK3), "human glandular kallikrein" (hK2), thyroglobulin, CA19-9 proteins, CA15-3, CA 125 ("CA" is the abbreviation for "cancer antigen"), angiotensin converting enzyme (ACE), cathepsin D, alphafoetoprotein, S100 protein, of the FGF-2 or EGF;

cleaved in their extracellular domain, in the case of membrane proteins whose extracellular domain is enzymatically cleaved and released into the extracellular medium (shed protein). For example, the HER2, EGFR (Epithelial Growth Factor Receptor) or MUC 1 markers are cleaved proteins; or released by the cell. The released molecules are, for example, non-membrane proteins secreted by the cell by different pathways of the secretory pathways, for example by budding, such as the protein CK 19 (Cytokeratin 19).

Exosomes are also part of the secretome of tumor cells. These are vesicles consisting of a lipid bilayer membrane surrounding a small cytosol. The cytosol of the exosomes may comprise proteins, double-stranded DNA, but also RNA (in particular mRNA, miRNA). Exosomes allow tumor cells to transfer oncogenic proteins and/or nucleic acids to modulate the activity of recipient cells, thereby playing a role in tumorigenicity, tumor growth, metastatic methods and drug resistance.

The method according to the invention may comprise one or more of the following characteristics, taken separately or in any technically feasible combination:

i) the particles are magnetic particles, advantageously paramagnetic, preferably superparamagnetic;

ii) the step of providing the droplets comprises:
the dispersion of the particles in a mass of fluid intended to form the droplets, and then
the dispersion of the mass of fluid in the form of droplets,
the formation in each droplet of at least one aggregate of particles defining an object elongated along a major axis, wherein the aggregate of particles is formed in each droplet after the dispersion;

iii) the target element is an element of the secretome of a tumor cell, iv) the target element is a peptide or protein of the secretome of a tumor cell;

v) the target element is a nucleic acid (DNA or RNA), in particular an miRNA of a tumor cell;

vi) the target element is an exosome of a tumor cell;

vii) at least some of the droplets comprise a producing entity capable of producing the target element, wherein the producing entity is a single tumor cell or an aggregate of tumor cells, and, in particular, a single circulating tumor cell (CTC), a disseminated tumor cell; (DTC), or an aggregate of CTCs or DTCs;

viii) the method comprises, before the measuring step, a step of orienting the main axis of the aggregate along a detection axis;

ix) the method comprises multiple measurement steps, with a step of orienting the main axis of the aggregate according to a different detection axis for each of the measurements;

x) the method comprises:
providing a device comprising a set of circulation of the droplet and a detection zone;
the transport of the droplet towards the detection zone, wherein the measurement within the droplet is carried out in the detection zone;

xi) the method comprises:
providing a device comprising a set of circulation of the droplet and a plurality of classification zones, and a means for selectively directing the droplet or portion of the droplet towards a classification zone,
the decision to classify the droplet or a portion of the droplet, wherein the decision consists in selectively choosing a classification zone from among the plurality of classification zones,
the transport of the droplet, or a portion of the droplet, to the classification zone of the droplet chosen in the decision step;

xii) at least one droplet comprises at least one target element, at least one capture element capable of capturing the target element and at least one signaling entity capable of forming a complex with the target element, possibly captured by the capture element method, wherein the method comprises measuring a signal indicating the relocation or concentration of the at least one signaling entity on the aggregate;

xiii) at least one droplet comprises at least one target element, at least one first signaling entity capable of forming a complex with the target element, and at least one second distinct signaling entity capable of forming a complex with the target element, wherein the method comprises measuring a signal indicating the concentration of each of the relocated signaling entities on the aggregate;

xiv) at least one droplet comprises at least one target element, at least one signaling entity capable of forming a complex with the target element, and at least one quantification entity capable of forming a complex with the target element, wherein the method comprises:
  measuring a signal representative of the concentration of the relocated signaling entity on the aggregate,
  measuring a signal representative of the concentration of the quantification entity relocated on the aggregate,
  determining the dissociation constant of the target element with the signaling entity from the signal ratio of the signaling entity relocated on the signal of the relocated quantization entity;

xv) at least one droplet comprises at least two distinct signaling entities, wherein each of the two signaling entities is able to form a complex with a distinct target element on the aggregate, wherein the method comprises measuring a signal indicating the concentration of each of the relocated signaling entities;

xvi) at least some of the droplets comprise a producing entity, wherein the producing entity is a cell capable of producing an element of the secretome of a tumor cell, wherein each member of the secretome of a tumor cell is a separate target element, while the measurement of the signal indicating the concentration of each of the relocated signaling entities allows quantification of the element(s) of the secretome;

xvii) the measurement of a physical parameter is a measure of radioactivity, colorimetry or fluorescence;

xviii) at least one of the droplets comprises a cell capable of secreting the target element and the method comprises an incubation step during which the target element is secreted in the droplet by the cell;

xix) the method comprises a step of measuring a physical parameter, locally at a first point located away from the aggregate in at least one of the droplets and the same physical parameter, locally at a second point in the vicinity of the aggregate in the same drop;

xx) the maximum particle size is less than 50% of the droplet diameter;

xxi) the droplet contains at least one signaling entity, and the measurement of the physical parameter depends on the position of the signaling entity within the droplet or with respect to the aggregate;

xxii) the producer entity produces a plurality of target elements selected from the group consisting of the elements, and, in particular, the proteins and peptides of the secretome of a tumor cell;

xxiii) the method comprises a step of determining at least one characteristic of the producing entity;

(xxiv) the classification decision step occurs after the measurement step;

xxv) the droplet contains superparamagnetic particles, wherein the droplet or portion of the droplet is directed towards the classification zone by a direction means selected from a magnetic field, an electric field, a dielectrophoresis, an electrocoalescence or a surface acoustic wave;

xxvi) a portion of the droplet is extracted by means of the magnetic force, wherein the extracted part forms an auxiliary droplet and contains the aggregate;

xxvii) the particles are functionalized with a capture element that is adapted to fix the target element, while each droplet comprises a signaling entity that is capable of fixing the target element;

xxviii) the signaling entity is fluorescent, radioactive or colored;

xxix) the measurement of a physical parameter is a measurement of chromometry, fluorescence or radioactivity;

xxx) the measurement of the physical parameter comprises the location of a fluorescence, chromometric or radioactivity signal within the droplet;

xxxi) the measurement of the physical parameter comprises the location of a signal of fluorescence, chromometry or radioactivity with respect to the aggregate within the droplet;

xxxii) the measurement of the physical parameter comprises measuring the intensity of a signal of fluorescence, chromometry or radioactivity within the droplet, preferably at the level of the aggregate;

xxxiii) the measurement of the physical parameter comprises the variation over time of the location and/or intensity of a signal of fluorescence, chromometry or radioactivity within the droplet, preferably at the level of the aggregate;

xxxiv) each droplet comprises at least two distinct signaling entities, wherein each of the two signaling entities is capable of forming a complex with a distinct target element on the aggregate, wherein each signaling entity is fluorescent in a separate fluorescence channel;

xxxv) the cell is a tumor cell, in particular a single tumor cell or an aggregate of tumor cells;

xxxvi) the cell, in particular the single cell or the aggregate of cells, is derived from a biological fluid and is selected from the group consisting of a circulating tumor cell and a disseminated tumor cell;

xxxvii) the measuring step comprises the measurement of the at least one physical parameter locally at a plurality of points situated in the droplet, wherein the measuring step preferably comprises the determination of the integral of the measured values within the droplet;

xxxviii) the measuring step is carried out in a microfluidic chamber without circulation of the droplets;

xxxix) the method comprises:
  providing a device comprising a set of circulation of the droplet and a plurality of classification zones, and a means for selectively directing the droplet or a portion of the droplet towards a classification zone,
  the decision to classify the droplet or a portion of the droplet, wherein the decision involves selectively choosing a classification zone from among the plurality of classification zones,
  the transport of the droplet, or of a portion of the droplet, respectively, towards the classification zone of the droplet chosen during the decision step,
  and optionally further harvesting the sorted droplet by transport to the classification zone, then lysing the sorted and harvested droplet, and then lysing the droplet and harvesting the living tumor cell contained in the sorted and lysed droplet.

xl) at least one droplet comprises at least two distinct signaling entities, wherein each of the two signaling entities is able to form a complex with a distinct target element on the aggregate, and wherein the method comprises measuring a signal indicating the concentration of each of the relocated signaling entities;

xli) at least some of the droplets comprise a single or aggregate of cells capable of secreting, cleaving or releasing one or more elements of the tumor cell secretome, wherein each element of the tumor cell secretome is a separate target element, wherein the measuring of the signal indicating the concentration of each of the relocated signaling entities, allows quantification of the element(s) of the tumor cell secretome.

The invention also relates to an apparatus for detecting and/or characterizing tumor cells, either singly or in the form of an aggregate of tumor cells, comprising:

a set of supplying a plurality of droplets contained in a carrier fluid, wherein at least one of the droplets comprises at least one aggregate of particles defining an object elongated along a main axis, wherein at least some droplets containing a single tumor cell or in the form of an aggregate of cells that is capable of producing a target element that is adapted to be fixed on the aggregate, characterized in that the apparatus comprises a set of measurement of a physical parameter that is characteristic of the fixing of a target element on the aggregate, wherein the apparatus optionally further comprises:

a set of circulation of the drop,
a set of classification decision of the drop,
a set of sorting of the droplet according to the classification decision.

The object of the invention is also a droplet for detection and/or characterization of tumor cells, either single or in the form of an aggregate of tumor cells, comprising a plurality of particles capable of forming an aggregate of particles defining an object elongated along a main axis, and a tumor cell, single or in the form of an aggregate of tumor cells, and optionally at least one target element of the tumor cell secretome, which is unique in the form of an aggregate of tumor cells, capable of being fixed on the aggregate.

The object of the invention is also a method for the preparation of detection droplets and/or characterization of tumor cells, either single or in the form of an aggregate of tumor cells, comprising:

dispersing, in a mass of fluid intended to form droplets, particles suitable for forming an aggregate defining an object elongated along a main axis, and a plurality of cells, wherein at least some of the cells are tumor cells capable of producing a target element of the secretome of a tumor cell, and then dispersion of the mass of fluid in the form of droplets, so that each droplet comprises a plurality of particles and at least some of the droplets comprise, in addition, a single cell or in the form of an aggregate of cells, and optionally forming in each droplet of at least one aggregate of particles defining an object elongated along a major axis, wherein the aggregate of particles is formed in each droplet after the dispersion.

BRIEF DESCRIPTION OF THE DRAWING FIGURE

Figure 2:
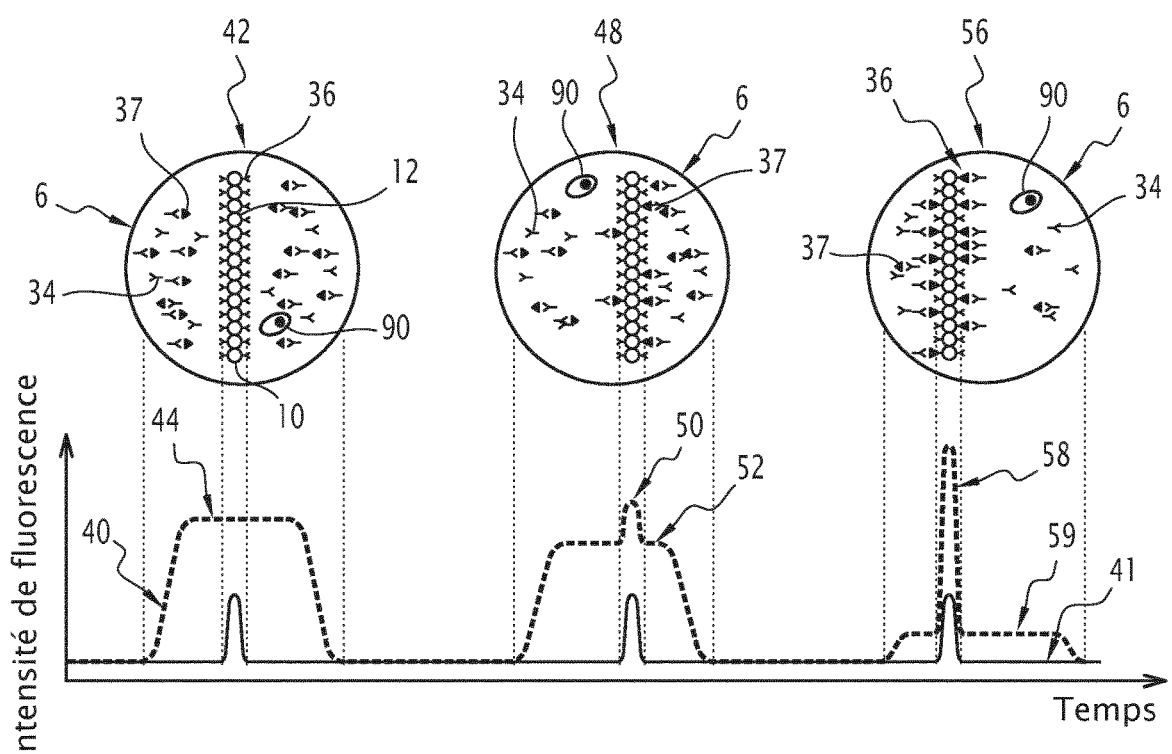
Figure 3:
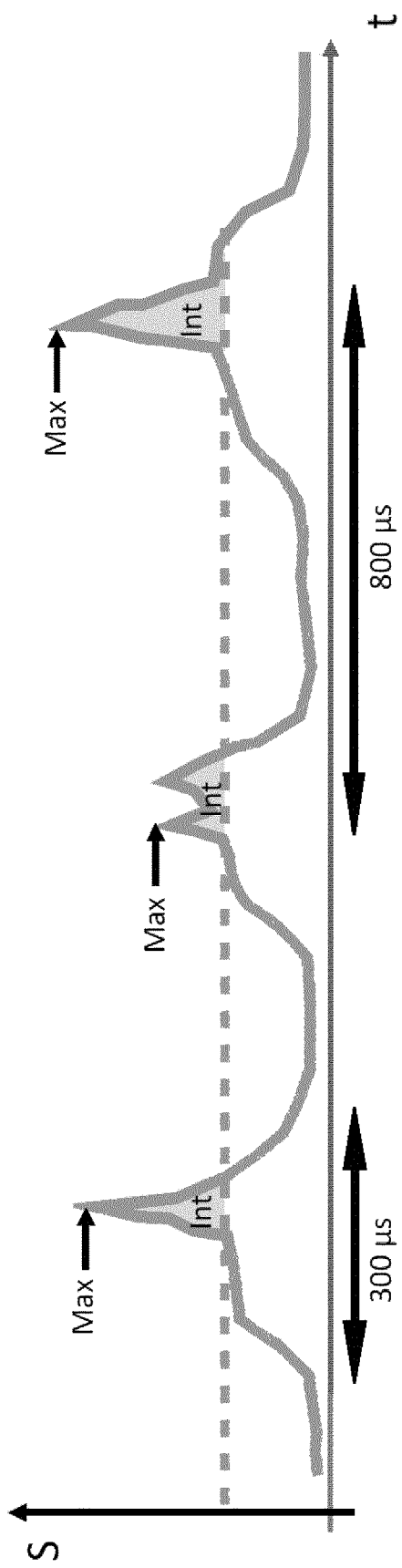
Figure 4:
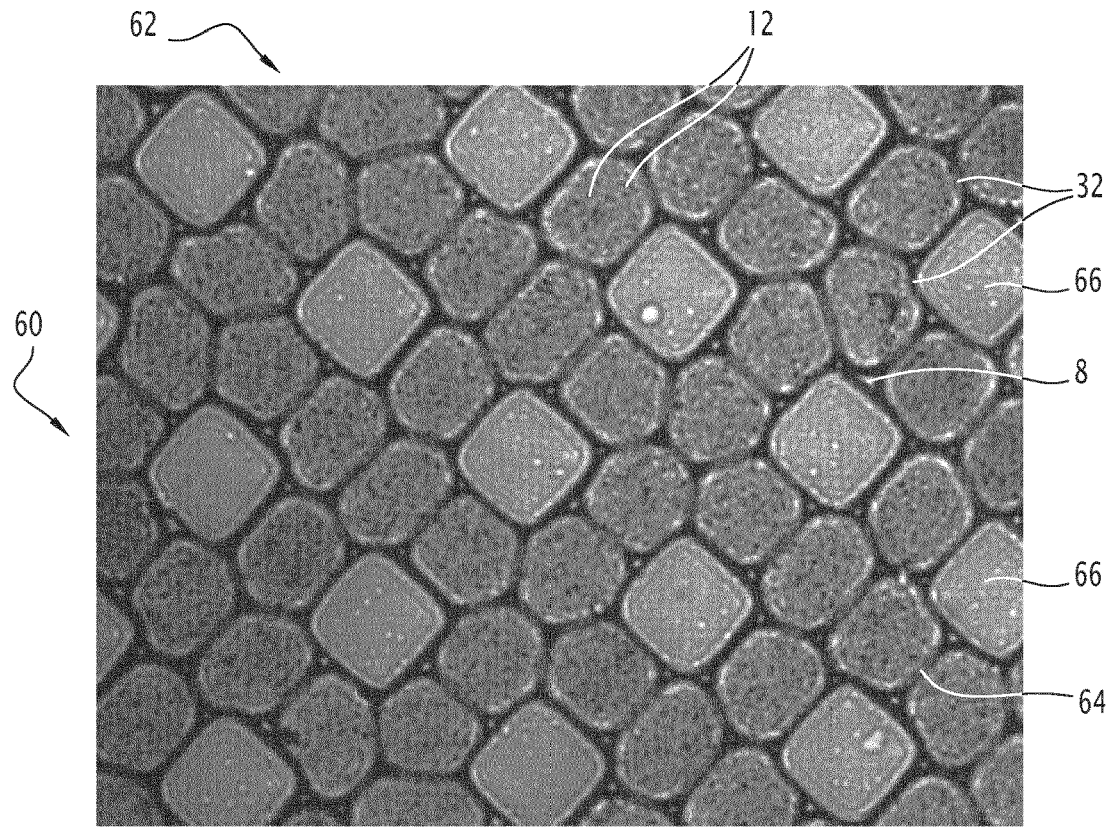
Figure 5:
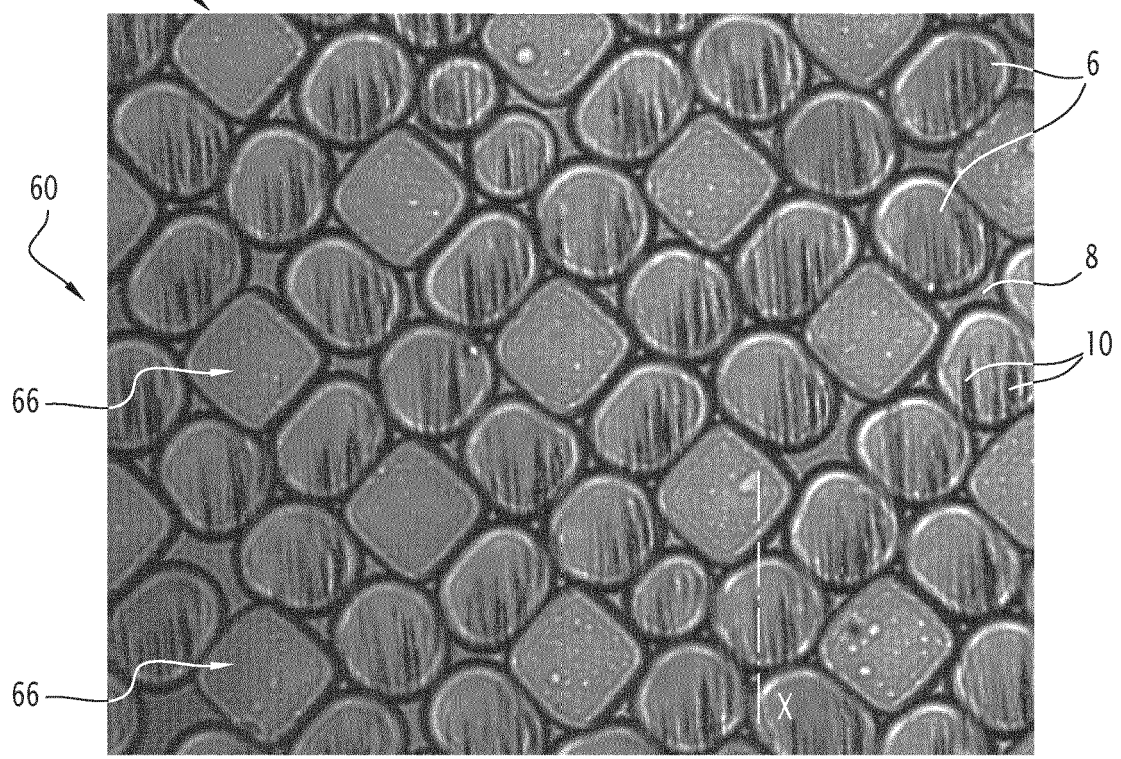
Figure 6:
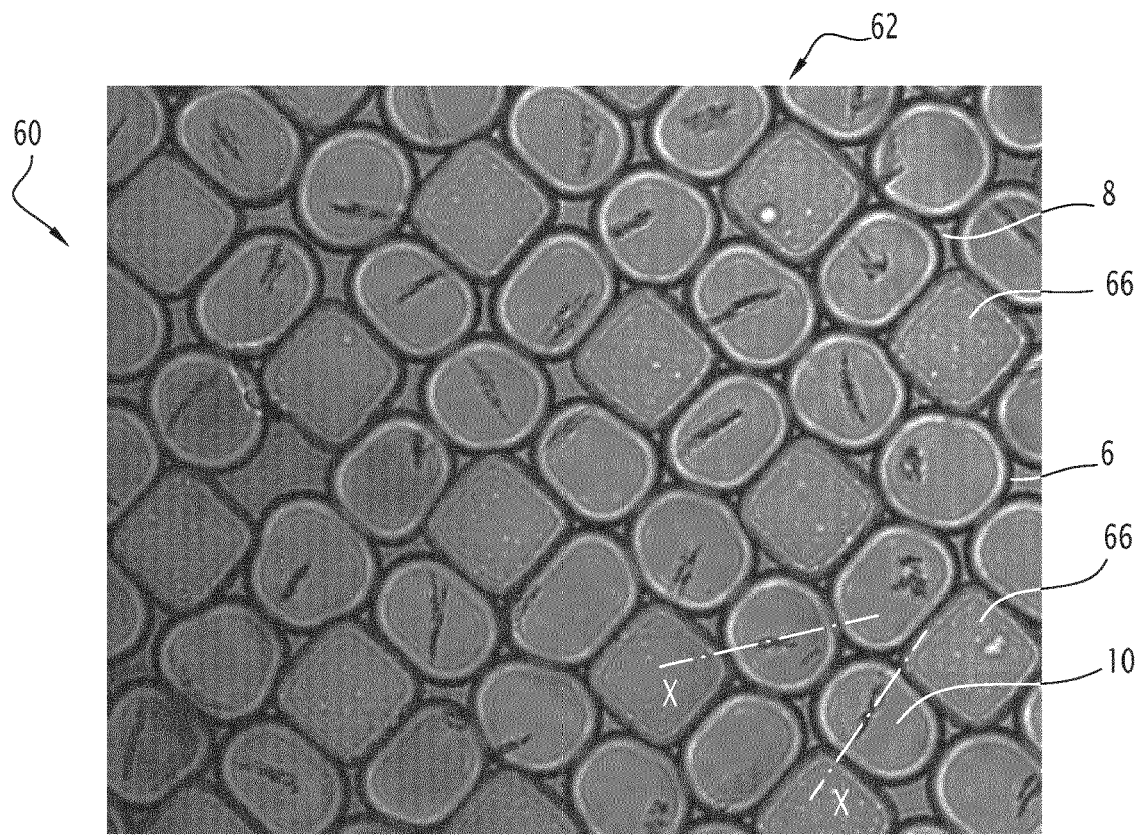
Figure 7:
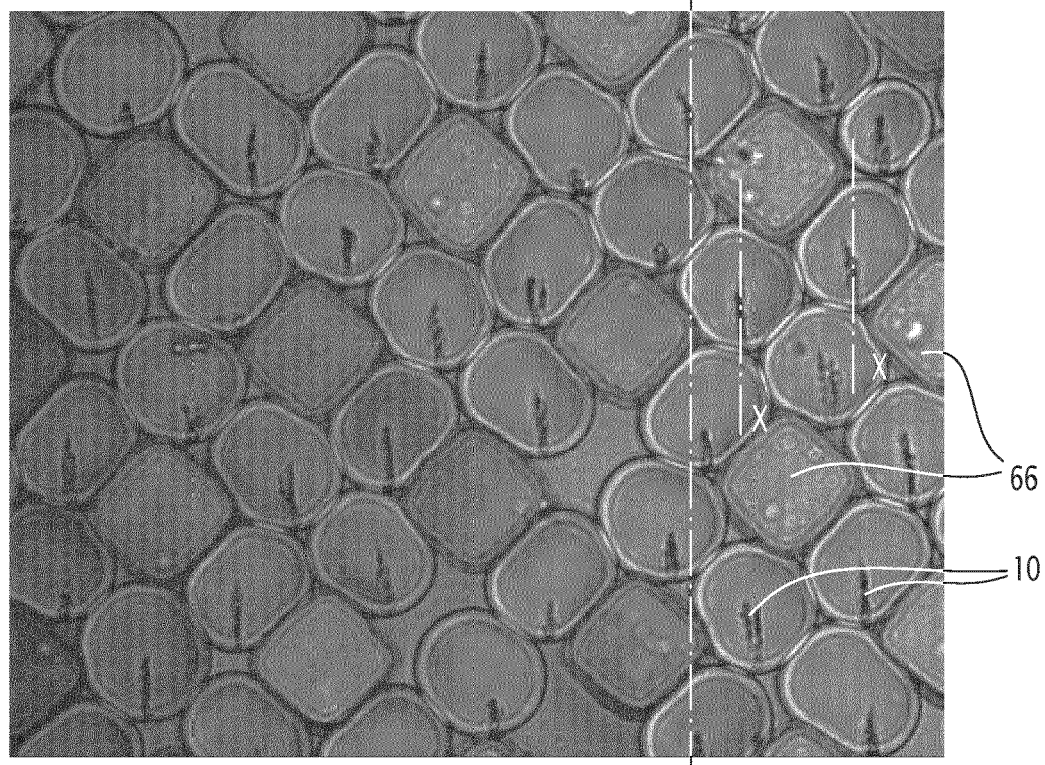
Figure 8:
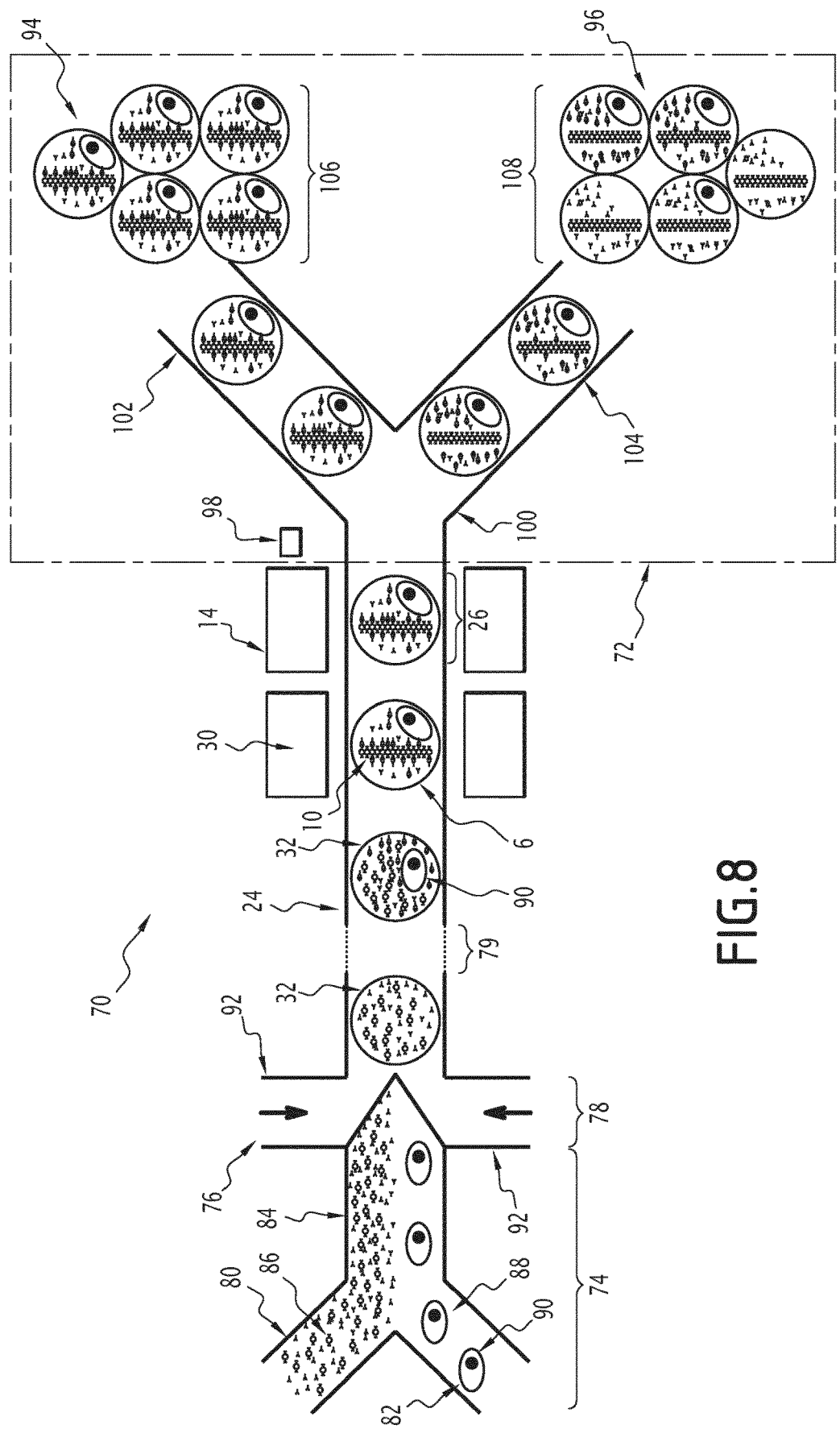
Figure 9:
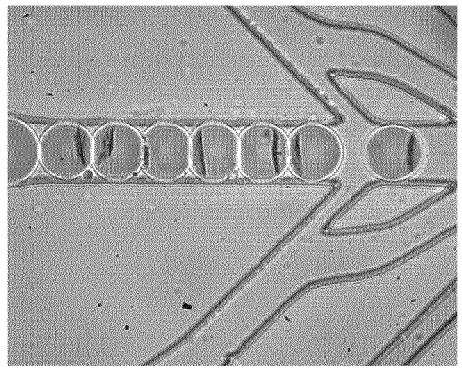
Figure 10:
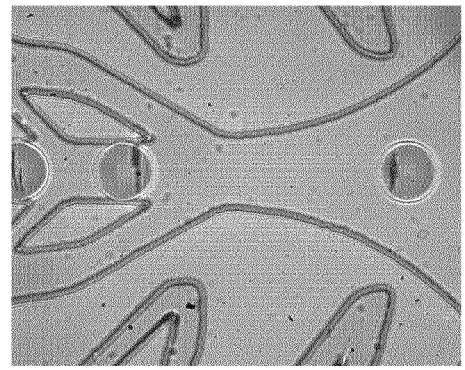
Figure 11:
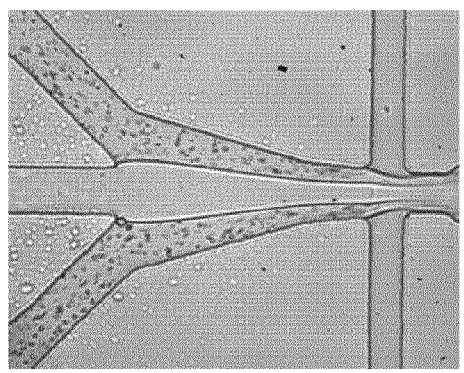
Figure 12:
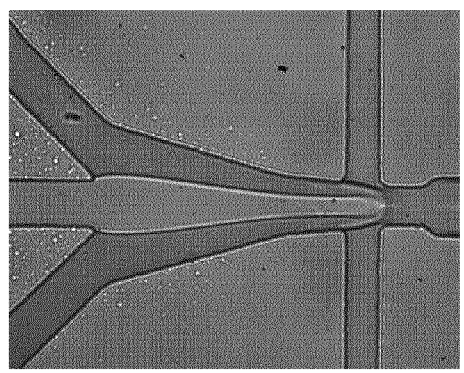
Figure 13:
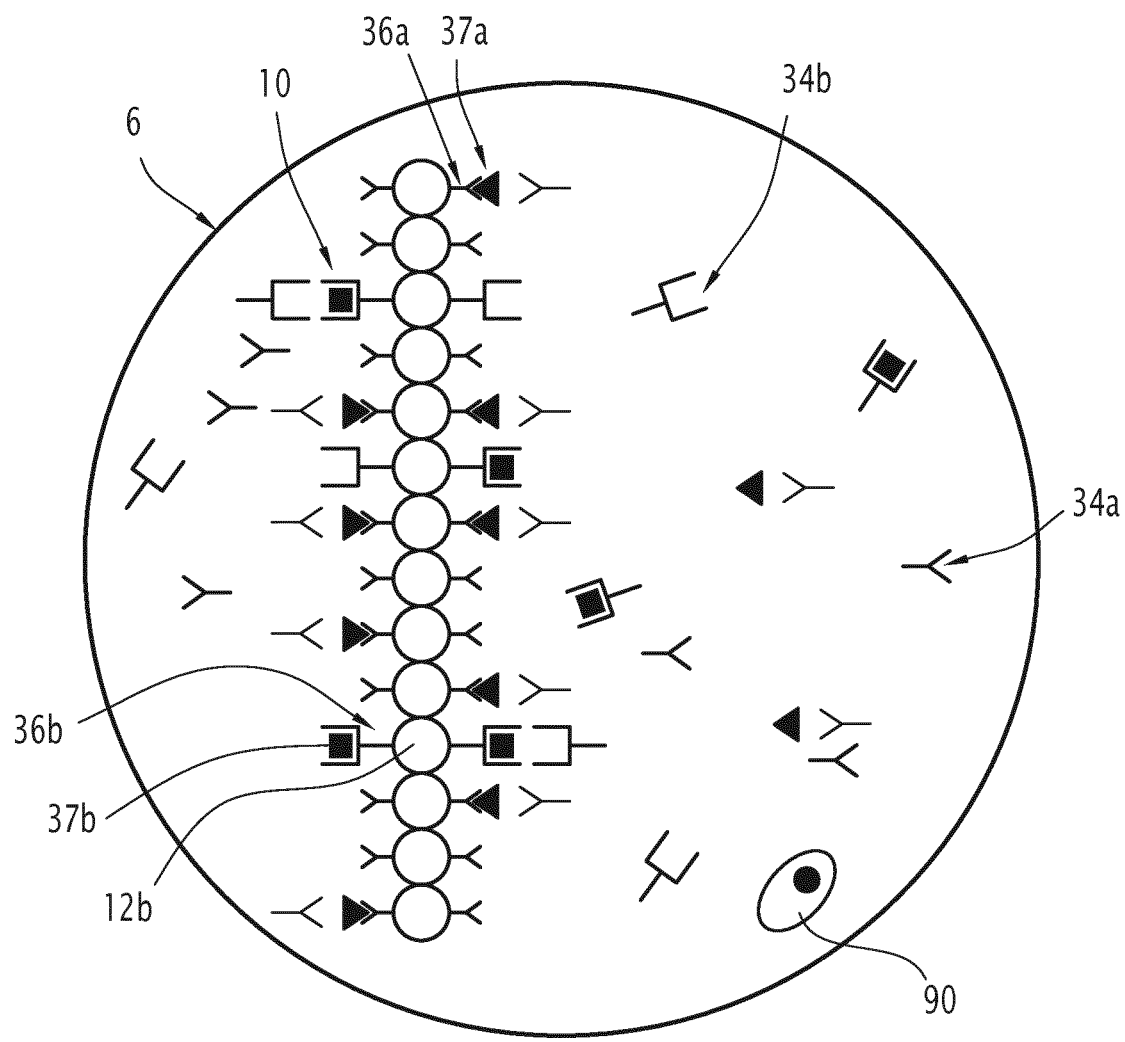
Figure 14:
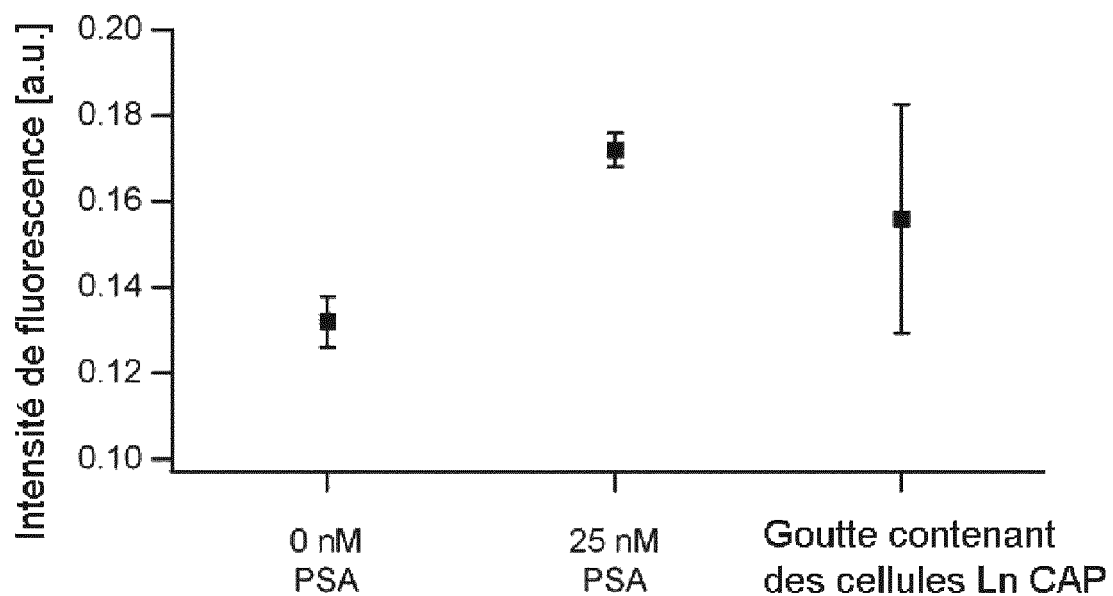
Figure 15:
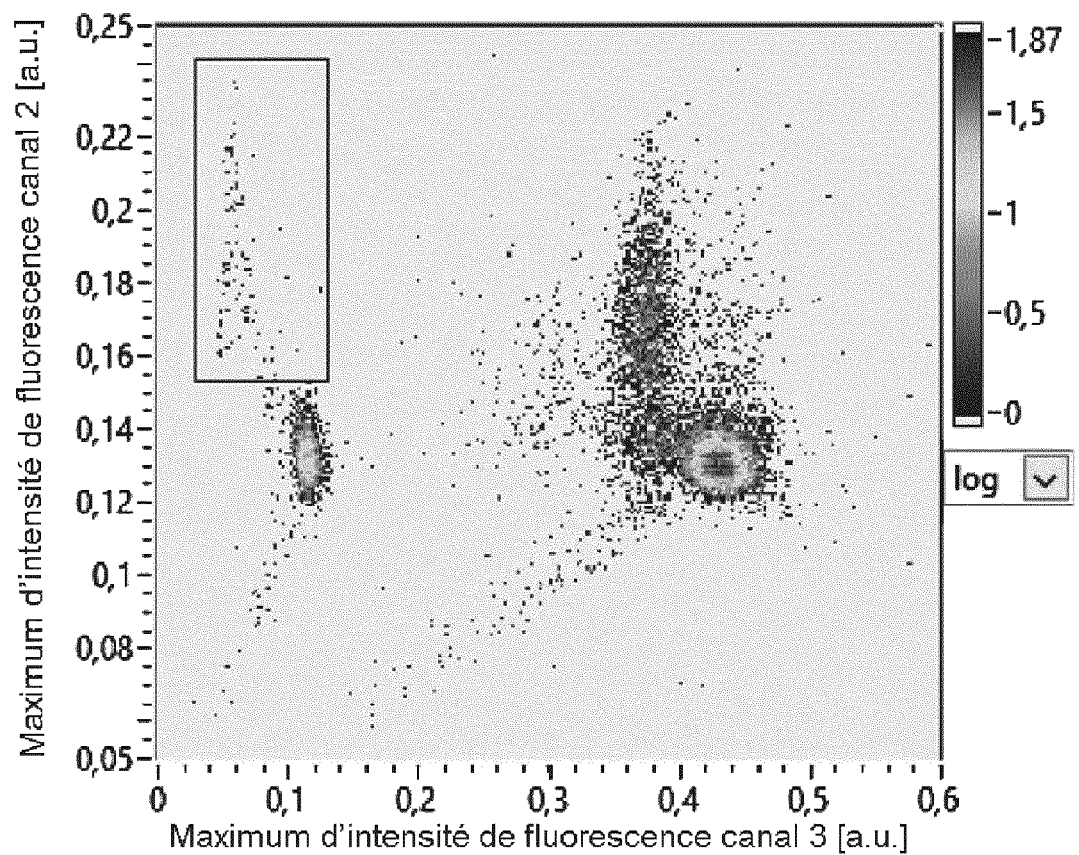
Figure 16:
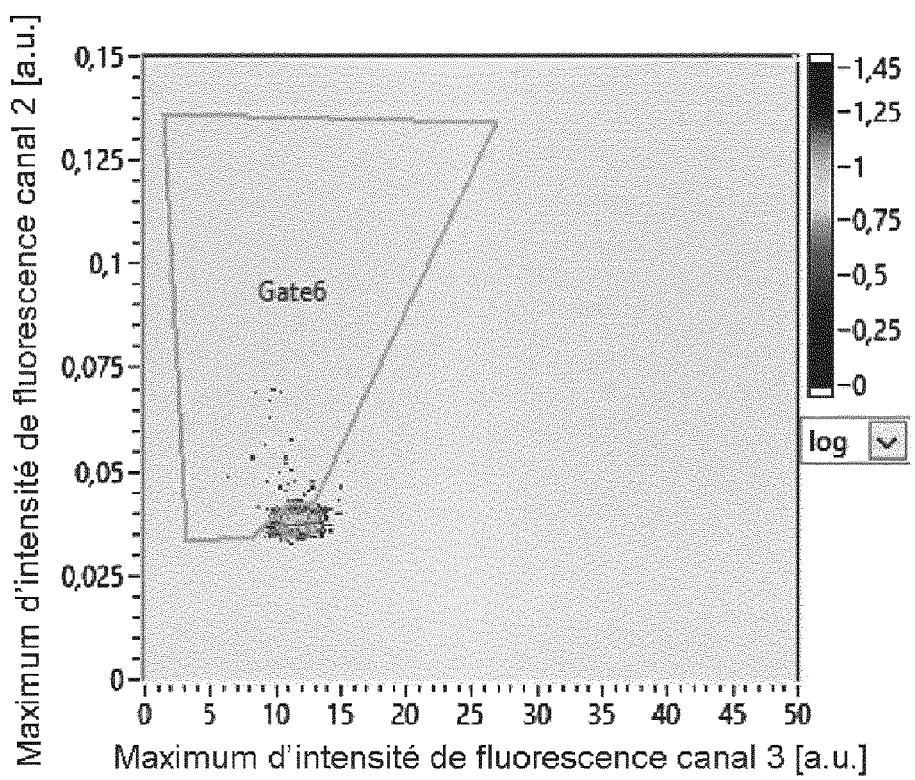
Figure 17:
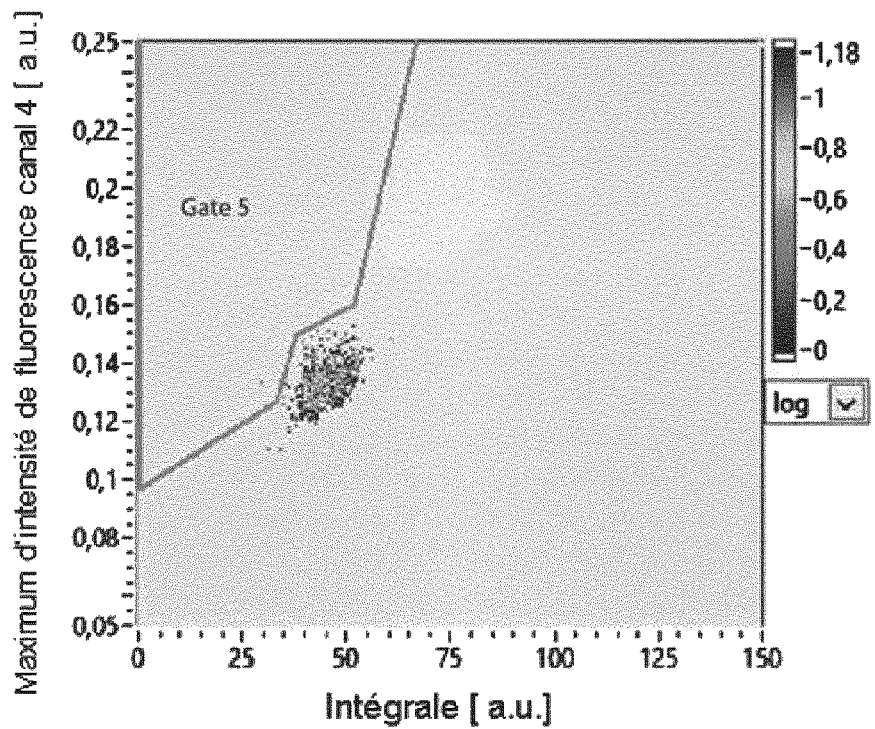
Figure 18:
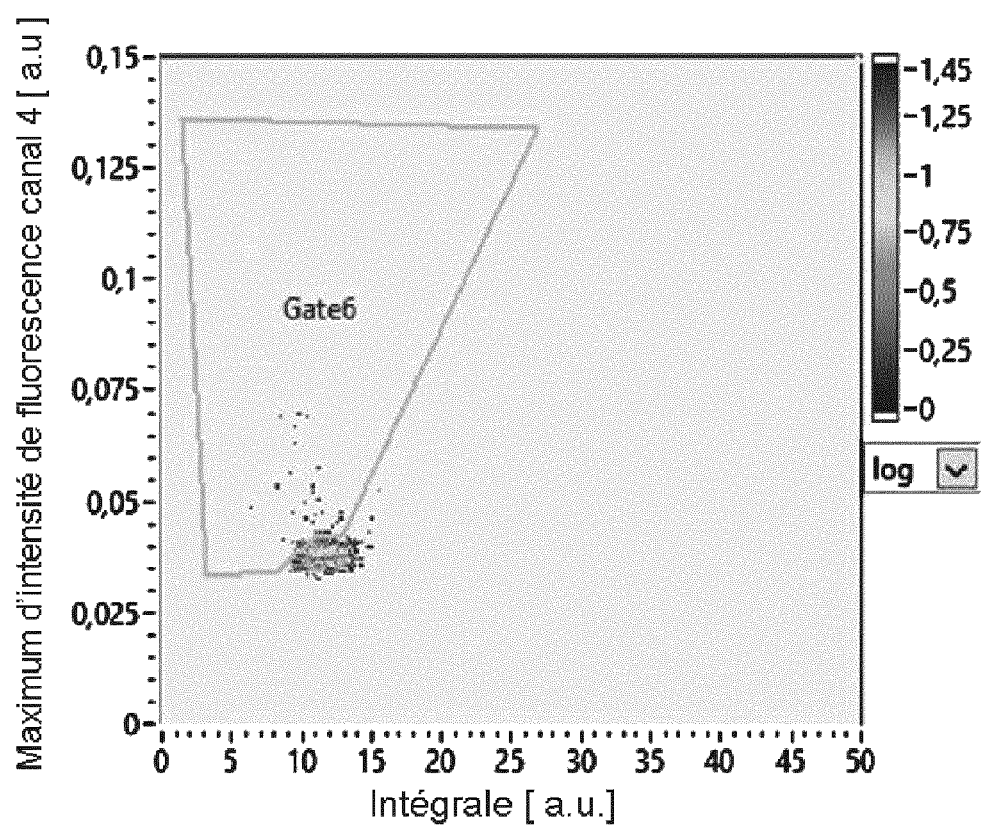
Figure 19:
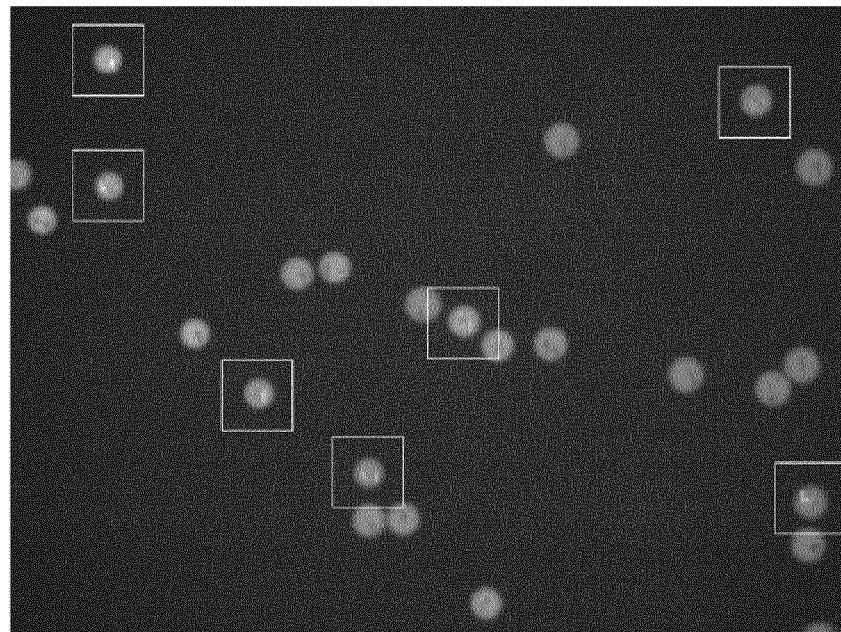
Figure 20:
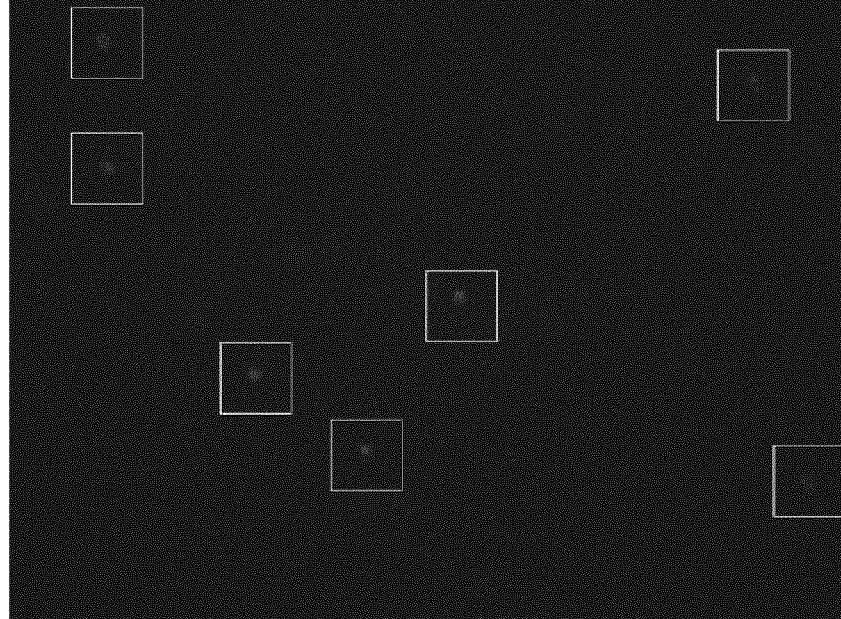
Figure 21:
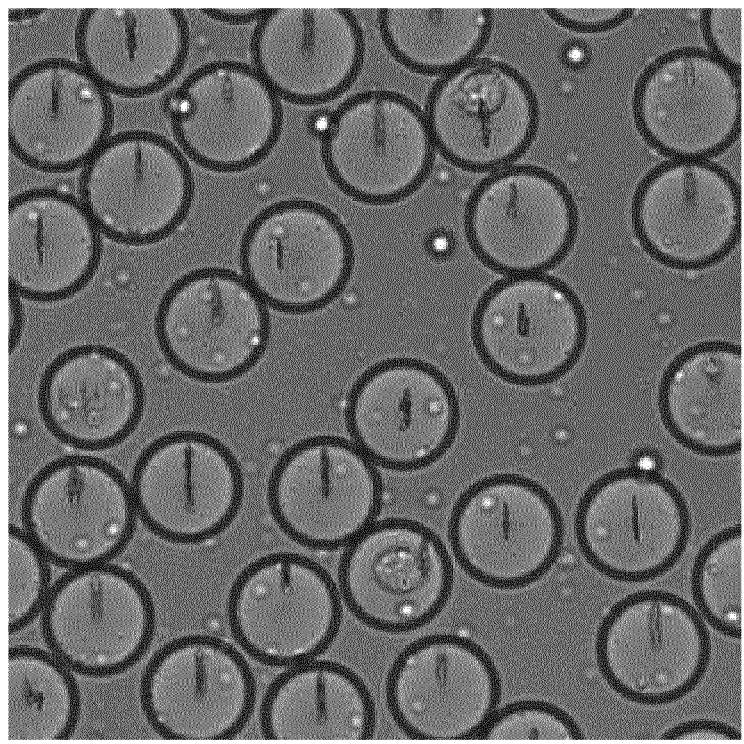
Figure 22:
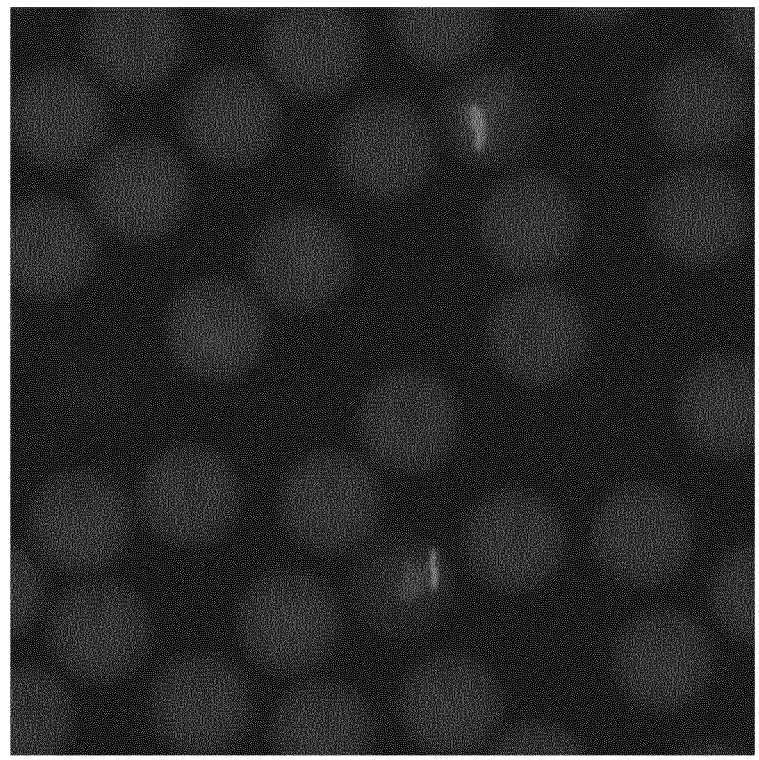
Figure 23:
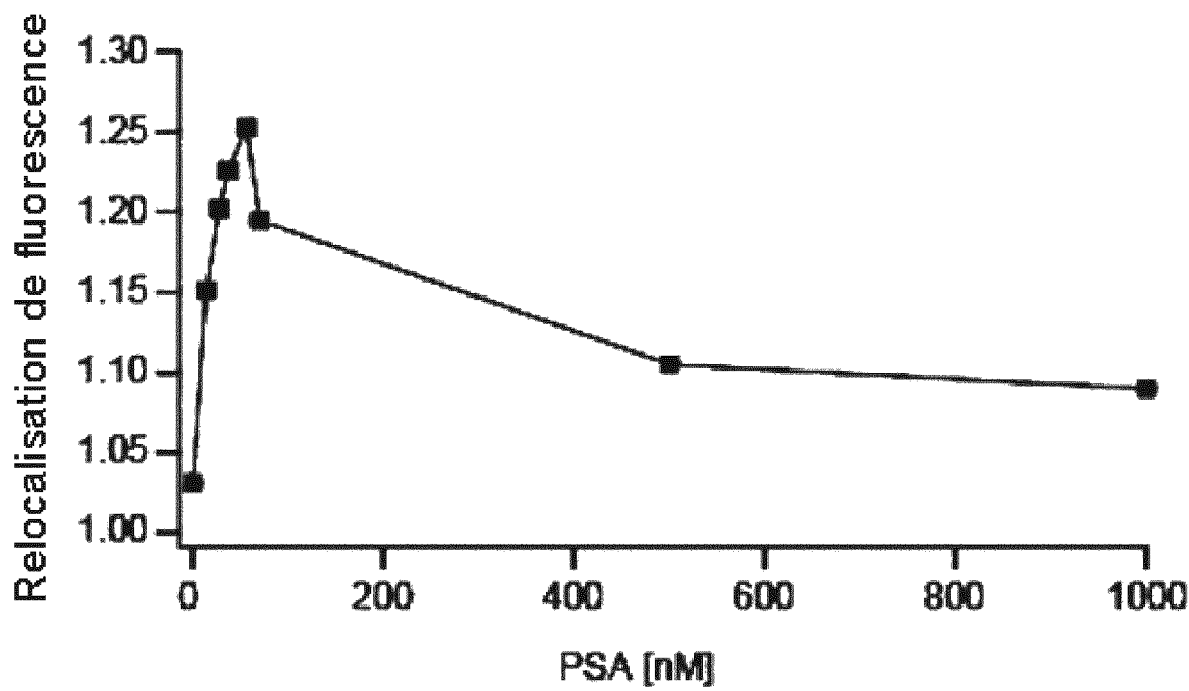
Figure 24:
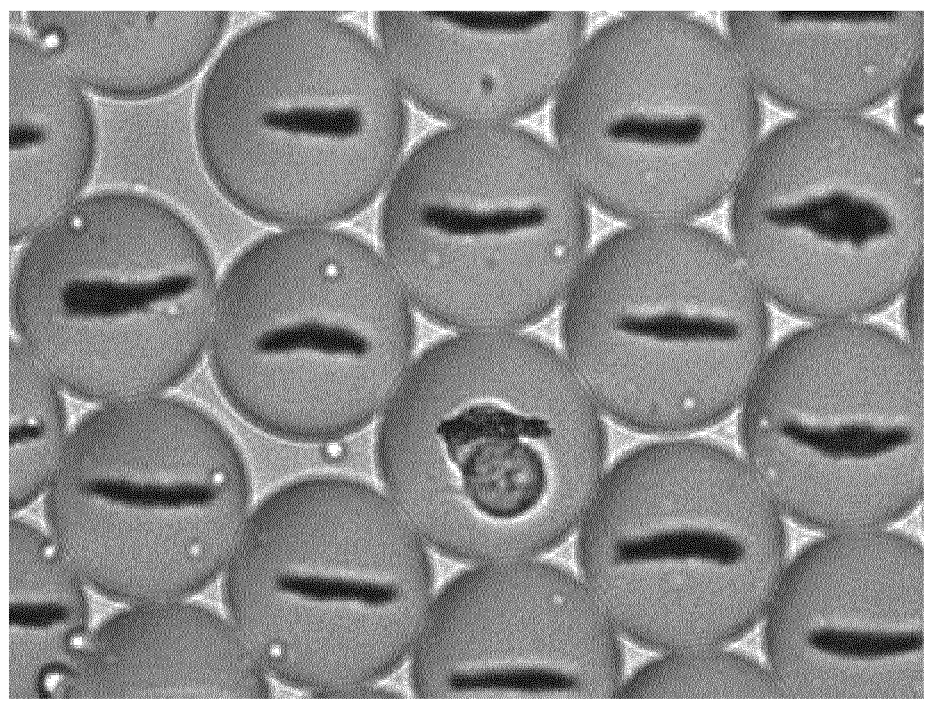
Figure 25:
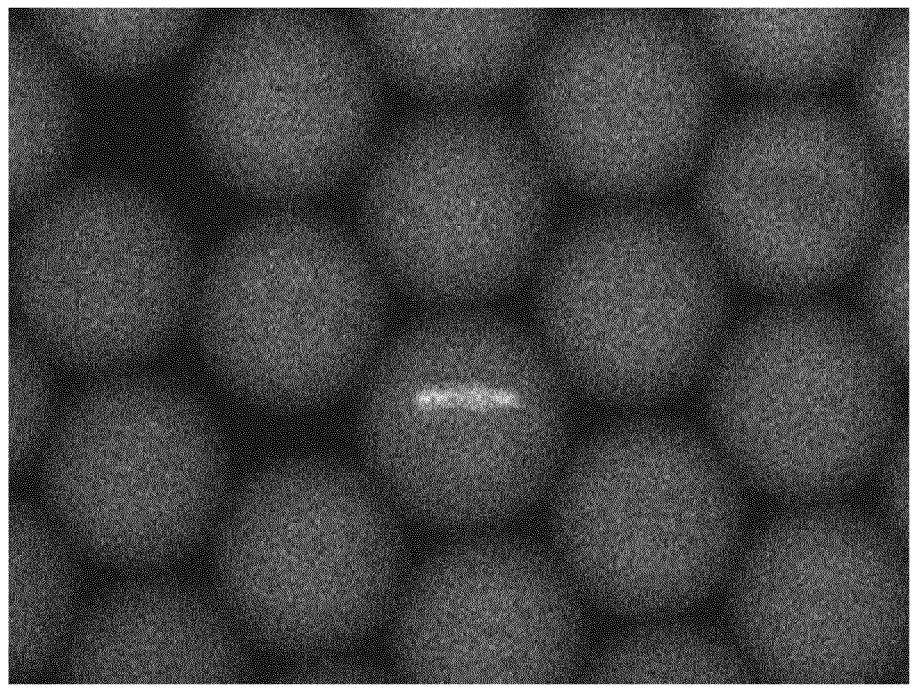
Figure 26:
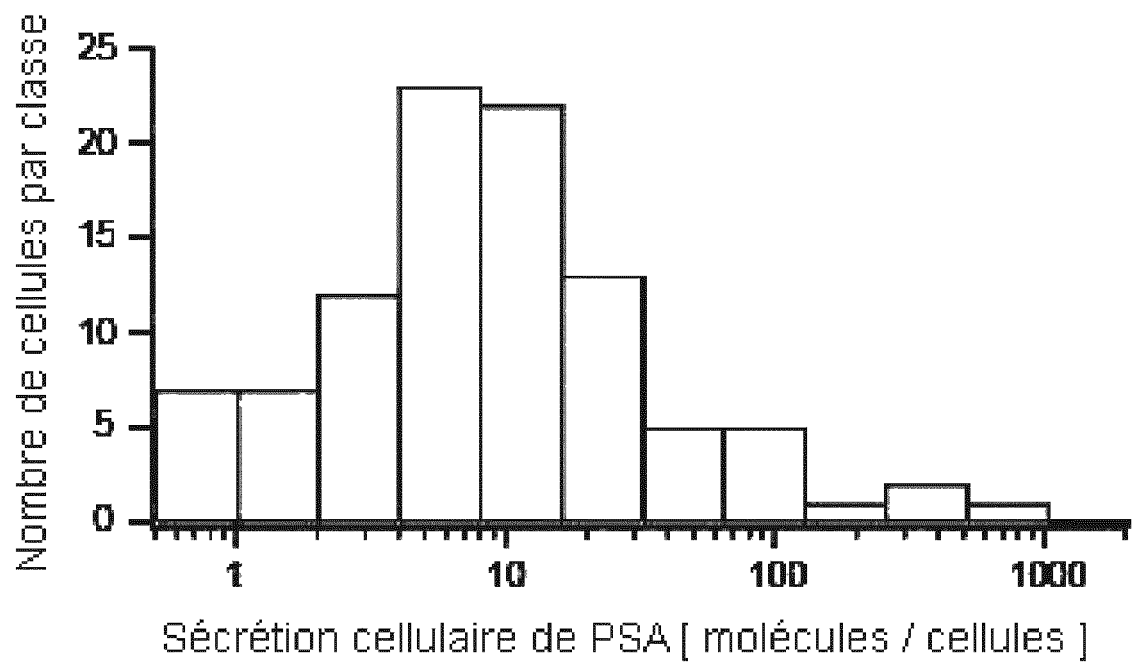

The invention, in particular according to the 'single cell' mode, will be better understood upon reading the description which follows, given solely by way of example, and with reference to the appended drawings, wherein:

FIG. 1 shows a schematic representation of the main elements of a first analysis apparatus according to the invention, FIG. 2 shows a schematic representation of a method element with the first apparatus, FIG. 3 shows a schematic representation of a method element with the first apparatus, FIG. 4 shows a photograph of part of a second apparatus according to the invention during different method elements according to the invention, FIG. 5 shows a photograph of part of a second apparatus according to the invention during different method elements according to the invention, FIG. 6 shows a photograph of part of a second apparatus according to the invention during different method elements according to the invention, FIG. 7 shows a photograph of part of a second apparatus according to the invention during different method elements according to the invention, FIG. 8 shows a schematic representation of a third apparatus according to the invention, FIG. 9 shows a set of spacings of droplets and reading, FIG. 10 shows a set of spacings of droplets and reading, FIG. 11 shows a device for generating droplets, FIG. 12 shows a device for generating droplets, FIG. 13 shows a schematic representation of a droplet during a step of implementing a method, FIG. 14 shows an example of an application of the method of the invention, FIG. 15 shows an example of an application of the method of the invention, FIG. 16 shows an example of an application of the method of the invention, FIG. 17 shows an example of an application of the method of the invention, FIG. 18 shows an example of an application of the method of the invention, FIG. 19 shows an example of an application of the method of the invention, FIG. 20 shows an example of an application of the method of the invention, FIG. 21 shows an example of an application of the method of the invention, FIG. 22 shows an example of an application of the method of the invention, FIG. 23 shows an example of an application of the method of the invention, FIG. 24 shows an example of an application of the method of the invention, FIG. 25 shows an example of an application of the method of the invention, FIG. 26 shows an example of an application of the method of the invention.

FIRST APPARATUS

A first apparatus 1 for analyzing the droplet content and for detecting and/or characterizing tumor cells, either singly or in the form of an aggregate of tumor cells, according to the invention, is represented in FIG. 1.

The apparatus 1 comprises a supply set 4 of a plurality of droplets 6 contained in a carrier fluid 8, wherein at least a portion of the droplets 6 comprises at least one aggregate 10 of particles 12 defining an object elongated along a main axis X.

An elongated object is an object having an elongated shape. An elongated shape has a length along the main axis that is greater than its length in a direction perpendicular to the main axis. Thus, a sphere is not elongated. For example, an oblong object, a cone, a rod or a non-spherical ovoid have elongated shapes.

The apparatus 1 further comprises a measuring set 14 of a physical parameter in the droplet.

The measurement set 14 is, for example, able to measure a physical parameter, locally at a first point 16 located at a distance from the aggregate 10 in at least one of the droplets, and the same physical parameter locally at a second point 18 in the vicinity of the aggregate 10 in the same droplet.

The apparatus 1 also comprises a device 20 comprising a circulation set 22, a circulation duct 24 and a detection zone 26.

The circulation set 22 is able to circulate each droplet 6 in the carrier fluid 8 in the duct 24 in the form of a train of successive droplets.

The supply assembly 4 comprises a loading set 28 and an aggregation set 30. The supply set 4 further comprises a spacing set 31.

The loading assembly 28 is capable of supplying a plurality of initial droplets 32 comprising a dispersion of particles 12, wherein at least one of the initial droplets 32 further comprises at least one target element 37 of the secretome of a tumor cell 90.

The spacing set 31 is able to space two successive droplets 6 of the droplet train, i.e. to increase the distance between two successive droplets. For example, the spacing set 31 has a carrier fluid inlet 8. Examples of spacing sets are shown in FIGS. 9 and 10.

The carrier fluid 8 is able to separate two successive droplets 6 of the droplet train to prevent their contact. Alternatively, the separation of droplets 6 may be performed by a mechanical device.

The fluid forming the internal phase of the droplets 6 and the carrier fluid 8 are substantially immiscible. For example, the droplets 6 comprise an aqueous internal phase while the carrier fluid 8 is an organic or oily phase.

The carrier fluid 8 is advantageously a fluorinated oil.

The carrier fluid 8 or the fluid forming the internal phase of the droplets advantageously comprises a surfactant capable of preventing the fusion of two droplets 6 upon contact, for example as described in the patent US 2010/0105112 or the EA surfactant from the company RainDance Technologies.

By "substantially immiscible" is generally meant that the solubility of the fluid forming the droplets in the carrier fluid 8, measured at 25° C. and at ambient pressure, is less than 1%.

The size of the droplets 6 is, for example, between 1 μm and 1000 μm. The volume of the droplets 6 is advantageously between 0.1 picoliter and 1 microliter.

The droplets 6 provided are substantially monodisperse. This means that the polydispersity of the droplets 6 is less than 5%.

In the example shown, the droplets 6 are spherical. Alternatively, the droplets 6 may be of an elongated shape along the circulation axis Y of the duct 24. Alternatively, the droplets 6 may be of a flattened puck shape along an axis perpendicular to the circulation axis Y.

Composition of the Droplets

Each initial droplet 32 comprises a base fluid, a dispersion of solid particles 12 in the base fluid, and a plurality of signaling entities 34. In addition, at least one initial droplet 32 comprises a cell 90, preferably a single tumor cell or an aggregate of tumor cells, and optionally at least one target element 37 of the tumor cell secretome.

As indicated above, the volume of a droplet 6 is advantageously between 0.1 picoliter and 1 microliter. The volume of a cell is about 1 picoliter. To encapsulate a single cell or a tumor cell aggregate, a droplet volume of between 20 and 150 picoliters, for example 20 to 50 picoliters, or 30 to 40 picoliters, for single cells, or even 30 to 40 picoliters, or advantageously chosen from 60 to 150 picoliters, or from 80 to 120 picoliters, in particular for cell aggregates.

The analysis of single cells and aggregates may be performed simultaneously or sequentially. For the simultaneous analysis, it is advantageous to use droplet volumes that are capable of encapsulating the cell aggregates (for example from 60 to 150 picoliters, typically about 100 pl). For sequential analysis, an integrated separation system (with techniques as described in Sajeesh and Sen, *Microfluidics and Nanofluidics* 2014, 17, 1-52) may be used to separate single cells and cell aggregates, followed by separate encapsulation of single cells, on the one hand, and cell aggregates, on the other hand. Alternatively, the single cells and cell aggregates may be encapsulated in droplets of small volumes (e.g. 20 to 50 picoliters), the cell aggregates sorted, and volume is subsequently added to the droplets containing the cell aggregates. The separation of the single cells and cell aggregates may also be performed prior to the implementation of the invention, and the single cells and cell aggregates are then analyzed sequentially and separately.

The droplet initially comprises the cell in the base fluid, typically a medium adapted to the culture of mammalian cells (and, in particular, of human cells) such as DMEM or RPMI, wherein the base fluid is then devoid of elements of the secretome of the cell. The secretome elements accumulate over time in the base fluid, by secretion, cleavage or release from the single cell.

The base fluid is so designed that a single cell or aggregate of cells in the droplet is capable of producing at least one target element of the secretome of a tumor cell that is capable of being bound to the aggregate, particularly when the single cell is a tumor cell, or when the cell aggregate contains or consists of tumor cells.

For example, each tumor cell 90, single or in the form of an aggregate of cells encapsulated in a droplet, is capable of producing a target element 37. In particular, the tumor cells 90 secrete, cleave or release secretome elements such as proteins or peptides, in particular proteins or peptides that mark the tumor. Tumor cells, single or in the form of an aggregate of cells, are, in particular, circulating tumor cells or disseminated tumor cells.

The particles 12 are intended to form the elongated aggregate 10. For example, the particles 12 are superparamagnetic particles that acquire a magnetic moment upon the application of a magnetic field. Superparamagnetism is the behavior of ferromagnetic or ferrimagnetic materials that occurs when they are in the form of small grains or nanoparticles. In grains of sufficiently small size, the magnetization may be reversed spontaneously under the influence of temperature. The term "magnetic particles" in the text refers to superparamagnetic particles.

The magnetic particles 12 are, for example, chosen from particles provided by the company Dynal (Life Technologies) or Ademtech or Miltenyi.

The particles 12 are, for example, nanometric. Thus, their maximum dimension is less than 1 μm and is, for example, between 50 nm and 1000 nm. The particles 12 are advantageously substantially monodisperse. For example, the variation between the maximum dimensions of the particles 12 is strictly less than 10%. The size and number of particles 12 per droplet 6 are chosen to form the desired number of aggregates. The maximum particle size 12 is less than 50% of the diameter of the droplet 6.

The concentration of particles 12 allows for colloidal stability.

The concentration of particles 12 in the droplets 6 is such that the particles 12 occupy between 0.1% and 5% of the volume of the droplet 6, for example 1.7%.

In one example, each droplet of 33 picoliters contains on average 500 particles 12 of 300 nm in diameter.

The particles 12 initially form a homogeneous dispersion in the initial droplets 32. They are distributed substantially uniformly in the volume of the initial droplet 32. Thus, the concentration of particles 12 is homogeneous over the entire initial droplet 32.

The particles 12 advantageously have a surface allowing the coupling of biological molecules, consisting of a surface material. For example, the particles 12 are covered with a polymer having COOH or $NH_2$ functions.

Advantageously, this surface material also makes it possible to limit the spontaneous aggregation of the particles 12 in the droplet.

Additionally, it may advantageously promote the stability of the aggregate 10, for example, via non-specific bonds between the material of a bead and its neighbor in the aggregate.

The particles 12 are advantageously functionalized. This means, in particular, that the surface material of the particles 12 comprises functional elements.

In the example shown, the functional elements comprise a capture element 36. The capture element 36 is, for example, able to capture the target element 37. The capture element 36 is able to bind indirectly to the signaling entity 34 via the target element 37.

The target element 37 secreted or released by the tumor cell, alone or in the form of an aggregate, or cleaved from the tumor cell, alone or in the form of an aggregate, is recognized by both the particle 12 capture elements 36, and by the signaling entities 34.

When the target element 37 is a secretome protein, peptide, lipid, carbohydrate or exosome, the capture elements 36 are advantageously constituted by a polyclonal antibody or a monoclonal antibody (in multiple copies) directed against, or specific to, the target element 37.

When the target element 37 is a target nucleic acid, such as an miRNA, of the secretome, the capture elements 36 are advantageously constituted by a nucleic acid (in multiple copies) hybridizing to the target nucleic acid, preferably a nucleic acid comprising or consisting of a sequence that is complementary to the sequence of the target nucleic acid. The capture nucleic acid is typically a DNA sequence, consisting for example of 10 to 200, 10 to 100, 10 to 50, or 10 to 30 nucleotides.

When the target element 37 is an exosome, the capture elements 36 are advantageously constituted by antibodies directed against a protein present in the membrane, or by lipids or sterols immobilized on a solid surface, for example particles, as described in Kuhn et al. (Integr Biol, 2012, 4, 1550-1555).

In the same manner, depending on the nature of the target element, the signaling entities 34 are advantageously constituted by (i) a polyclonal antibody or a monoclonal antibody (in multiple copies) directed against or specific to the target element 37, wherein the monoclonal or polyclonal antibody is detectably marked, or (ii) a signaling nucleic acid (multiple copies) hybridizing to the target nucleic acid, preferably a nucleic acid comprising or consisting of a sequence complementary to the sequence of the target nucleic acid, wherein the signaling nucleic acid is detectably marked.

The marker may typically be a radioelement, a chromophore compound, a fluorophore, or an enzyme coupled directly or indirectly to the antibody or nucleic acid.

The presence of these target elements 37 in the droplet 6 allows the relocation of the signaling entities 34 to the aggregate 10, as will be described later.

On the other hand, when the single cell is not a tumor cell, when the cell aggregate does not contain a tumor cell, or when the single cell or cell aggregate does not produce the target element 37 of the tumor cell secretome, or not in sufficient quantity, the signaling entities 34 do not relocate on the aggregate 10.

The relocation of the signaling entities 34 to the aggregate thus makes it possible to detect that the cell, single or in the form of an aggregate, secretes, cleaves or releases the target element 37 and therefore:

characterize that the cell is a tumor cell if the target element is a specific marker of the tumor cells or of a tumor cell type, and/or characterize that the target element 37 is part of the secretome of the cell.

When several different target elements 37 are sought, different signaling entities and different capture elements are associated. Their relocation is detected independently by different signaling entities and different capture elements, for example on different fluorescence channels.

Each relocation of a distinct signaling entity 34 associated with a distinct target element makes it possible to detect that the cell secretes, cleaves or releases the associated target element 37.

The aggregation set 30 is capable of generating an aggregation of the particles 12 along a main axis X.

The aggregation set 30 comprises, for example, two magnets 38 located on either side of the duct 24. The magnetic field is non-parallel to the circulation axis Y and advantageously perpendicular to the circulation axis Y. The aggregation assembly 30 allows the formation of an elongated aggregate in each droplet 6.

In one embodiment, the magnets 38 are permanent.

Alternatively, the aggregation set 30 may comprise a non-permanent magnet.

Alternatively, the aggregation set 30 is able to switch from an active mode to an inactive mode in order to generate elongated aggregates only in some droplets.

Each aggregate 10 of particles 12 comprises, for example, a column oriented along a main axis X. The height of the column is advantageously between 50% and 100% of the diameter of the droplet 6. Its width is, for example, less than 60% of its height.

In addition, the aggregate set 30 is, for example, able to orient the aggregate along a preferred axis. In the example shown, the axis X of the aggregate 12 is perpendicular to the circulation axis Y of the droplets 6 in the circulation duct 24.

The measuring set 14 comprises, for example, a laser line capable of optically measuring the intensity of the fluorescence along a line extending along an axis X' perpendicular or inclined with respect to the axis of circulation Y.

The measurement set 14 is able to carry out the measurement within the droplet in the detection zone 26.

The axis X' of the laser line is advantageously parallel to the axis of the aggregate X in the detection zone 26.

When the flow rate of the carrier fluid 8 is constant, the measurement as a function of time of the signal obtained by the laser line corresponds to a spatial scan of the droplet 6 passing in front of the laser line. This makes it possible to take several measurement points successively and, in particular, at least a first measurement point 16 located at a distance from the aggregate 10, and a second measurement point 18 located closer to the aggregate 10 in the vicinity of the aggregate 10.

In practice, a plurality of successive measurement points are taken over the entire longitudinal dimension of the droplet 6 during its gradual passage with respect to the measuring set 14.

In the example shown in FIGS. 1 to 3, the signaling entity 34 is fluorescent.

The circulation duct 24 is intended to allow the circulation of the droplets 6, 32 along the circulation axis Y in a direction of flow passing from the supply set 4 to the measurement set 14.

The circulation duct 24 advantageously has an internal diameter less than or equal to 1 mm.

The circulation duct 24 is elongated along the circulation axis Y. The circulation duct 24 has an inner cross-section of rounded contour such as circular or elliptical, or a polygonal contour such as rectangular.

The circulation duct 24 is, for example, defined in a translucent material allowing measurement of optical parameters by the measurement set 14. Alternatively, the circulation duct 24 may define at least one transparent measurement window in the detection zone 26.

The walls of the circulation duct 24 are sealed against the carrier fluid 8.

For example, the circulation duct 24 is defined in a capillary tube of internal dimension advantageously less than 1 mm. Alternatively, the circulation duct 24 may be defined in a microfluidic chip.

The set of circulation droplets 22 is intended to move the droplets 6, 32 one by one in the duct 24 in the direction of circulation.

The circulation set 22 comprises, for example, a syringe pump for applying controlled flow rates to the carrier fluid 8. Alternatively the circulation set 22 may comprise a pressure controller.

Analysis Method with the First Apparatus

A first analysis method according to the invention implemented in the first apparatus 1 will now be described.

An apparatus 1 as previously described is provided. Initial droplets 32 as described above are prepared in a carrier fluid 8.

Preferably, the particles 12 are dispersed homogeneously in each initial droplet 32. Given the small size of the individual particles 12 compared to the initial droplets 32, each initial droplet 32 contains a high number of individual particles 12, for example greater than 10. The probability of obtaining an initial droplet 32 devoid of particles 12 is very low, or even zero.

Some droplets 6 comprise a single tumor cell 90 secreting, releasing or cleaving the target element 37.

Preferably, the signaling entities 34 are dispersed homogeneously in each initial droplet 32.

Within the initial droplet 32, bonds are formed between the elements having particular affinities.

In one example, each target element 37 binds to a signaling entity 34 and a capture element 36. The signaling entity 34 is thus relocated to a particle 12.

In the following, "relocated" entities are entities linked to the aggregate 10.

The initial droplets 32 are circulated together with the carrier fluid 8 in the duct 24 by the circulation set 22.

At least one initial droplet 32 is conducted to the aggregation set 30. An aggregate 10 of particles 12 defining an object elongated along a major axis X is formed by the aggregation set 30 in the initial droplet 32.

Preferably, when the particles 12 are magnetic particles, they align along the main axis X during their passage opposite each magnet 38 of the aggregation set 30.

The droplet 6 comprising the elongated object is led to the detection zone 26. A physical parameter is measured locally by the measuring set 14 at least at a first point 16 in at least one of the droplets 6.

In a particular embodiment, a physical parameter is measured locally by the measurement set 14 at least at one first point 16 in at least one of the droplets 6, and the same physical parameter is measured locally at least at one second point 18 in the vicinity of the aggregate 10 in the same droplet 6 by the measurement set 14.

Measurement

FIG. 2 shows, by way of illustration, different measurements obtained for different droplets 6. The graph shows the fluorescence intensity measured by the laser line as a function of time.

The fluorescence intensity is measured in a wavelength range characteristic of the signaling entity 34. In the example, the fluorescence intensity is further measured in a wavelength range that is characteristic of the particles 12, wherein the particles 12 are fluorescent. The aggregate 10 is thus more easily identifiable.

The fluorescence intensity 40 corresponding to the fluorescence of the signaling entity 34 measured on the laser line, is shown in dashed lines in FIG. 2 for various droplets 6.

The fluorescence intensity 41 corresponding to the fluorescence of the particles 12 is presented in solid lines in FIG. 2 for different droplets 6.

The measurement step comprises determining the physical parameter locally at a plurality of points in the droplet. It also advantageously comprises an accumulation of the values measured at a plurality of points, for example the determination of the integral of the measured values within the droplet 6.

The first droplet 42 shown is a droplet 6 in which the different signaling entities 34 have not been relocated to the particles 12. The distribution of the signaling entities 34 is homogeneous within the droplet 6. A fluorescence intensity signal in the form of a plateau 44 is measured.

The second droplet 48 shown is a droplet 6 in which a portion of the signaling entities 34 has been relocated to the particles 12. In fact, these signaling entities 34 are linked to a target element 37 captured by the capture element 36. The fluorescence intensity in the vicinity of the aggregate 10 is therefore greater than in the rest of the droplet 6. A fluorescence intensity signal having a peak 50 in addition to a plateau 52, is measured.

The height of the plateau 52 of the second droplet 48 is smaller than the height of the plateau 44 of the first droplet 42 because fewer signaling entities 34 are free away from the aggregate 10.

The third droplet 56 shown is a droplet 6 in which a larger proportion of the signaling entities 34 has been relocated to the aggregate. A fluorescence intensity signal has a peak 58 and a plateau 59. The height of the measured peak 58 is greater than the height of the peak 50 measured in the second droplet 48 because more signaling entities 34 are captured by the particles 12 and are, therefore, located in the vicinity of the aggregate 10.

FIG. 3 shows the choice of parameters that are useful for estimating the concentration of relocated signaling entities 34.

In FIG. 3, which shows the signal S during the time t, we see three droplets containing one (on the left and on the right) or two aggregates (in the center) which have a higher signal peak. The useful parameter may be the maximum of the signal (indicated Max) or the integral of the signal with respect to a given threshold (Int).

A first method consists in estimating this concentration by the maximum value of the signal (Max) in each droplet 6, i.e. the height of the signal peaks relocated on the aggregate.

A second, more precise method consists in calculating the integral of the signals (Int) for each droplet 6 beyond a threshold set by the user, as shown for example in FIG. 3. This method may be more interesting in order to limit the dispersion of the signal.

Both of these signal treatment methods may be performed in real time.

Other methods, for example combining these approaches, could be applied, for example to measure both the relocated and non-relocated signaling entity 34.

The invention also makes it possible to measure the concentration of the target element 37 in the droplet 6.

A simple case for doing this is to consider the case where:
- the capture element 36 is in sufficient quantity and of sufficient affinity for the target element 37 to capture at least more than 90% of the target element on the aggregate, advantageously all of it;
- the concentration of the signaling entity 34 is greater than that of the target element 37 and the dissociation constant Kd between the signaling entity 34 and the target element 37 is less than the concentration of the target element 37, advantageously by a factor greater than 10. This is typically the case when using optimized assay reagents such as subnanomolar Kd monoclonal antibodies, and it is desired to detect target element concentrations 37 greater than nanomolar.

"Nanomolar" is understood to mean 1 nanomole/L.

Under these particular conditions, the presence of each target element 37 gives rise to the formation of a capture element complex 36—target element 37—signaling entity 34. The concentration of the target element 37 is therefore proportional to the signal of the signaling entity 34 relocated to the aggregate 10. Other conditions make it possible to perform this quantification and will be obvious to those skilled in the art by modifying the concentrations and affinities of the capture elements 36, or of the signaling entities 34 for the target element 37.

Application: Tumor Cell Detection

If the target element is a specific marker of the secretome of a tumor cell, its detection may be sufficient to detect encapsulated single or aggregated tumor cells.

If the target element is a characteristic marker of the secretome of a tumor cell, but not specific to tumor cells, its detection in combination with one or more other target elements constituting characteristic markers of the secretome of a tumor cell may make it possible to detect that the single encapsulated cell is a tumor cell.

Following the measurement step, information on the tumor nature of the cell encapsulated in the droplet, as a single cell or in an aggregate of cells, is obtained.

This information makes it possible to know which droplets must be retrieved downstream for other measurements or uses.

The method thus makes it possible to detect isolated tumor cells from a biological sample comprising heterogeneous cells. Non-tumor cells or tumor cells that do not produce the target element are identified because their droplet does not contain the target element and the signaling entities have not been relocated. This method thus makes it possible to detect or even count tumor cells in a population of cells from a biological sample.

Application: Tumor Cell Characterization

If the encapsulated single cells are only tumor cells, the measurement of the target element may make it possible to obtain information relating to the production of the target element by the single tumor cell, for example its concentration.

If the aggregate of encapsulated cells contains one or more tumor cells, the measurement of the target element may make it possible to obtain information relating to the production of the target element by the aggregate of cells, for example its concentration.

Following the measurement step, information is obtained on one or more characteristics of each tumor cell encapsulated in the droplet, or of each aggregate containing one or more tumor cells encapsulated in the droplet.

This information makes it possible to obtain information on the heterogeneity or the properties of the tumor cells.

Application: Detection and Characterization of Tumor Cells

During the measurement, information may be obtained both on the tumor nature of the cell and on characteristics of the tumor cell, for example by detecting the target element and measuring its concentration.

In addition, by detecting multiple target elements, a large amount of information may be obtained simultaneously. For example, certain target elements are tumor markers and other elements of the secretome, such as proteins or peptides, are not specifically tumor markers.

Following the measurement step, information on characteristics of each tumor cell encapsulated in the droplet is obtained.

This information makes it possible to obtain information on the heterogeneity of the tumor cells and various mechanisms.

Second Apparatus

FIGS. 4 to 7 show a portion of a second apparatus 60 according to the invention.

This second apparatus 60 differs from the first apparatus 1 in that the device 20 comprises a chamber 62. The chamber 62 comprises a plurality of circulation passages 64 and a plurality of separation traces 66.

Other chambers are possible. In one variant, chambers do not comprise separation traces as described in document PCT/FR2009/051396.

The chamber 62 is intended to store a plurality of droplets 6 in a carrier fluid 8 during an aggregation step or an orientation step and during the measurement step.

The measurement unit of the second apparatus 60 differs from the measurement unit 14 of the first apparatus 1 in that it is able to measure the physical parameter simultaneously on several droplets 6 present in the chamber 62.

FIG. 4 shows the chamber 62 containing initial droplets 32 in a carrier fluid 8. The dispersion of the magnetic particles 12 is visible. FIG. 5 shows the same chamber 62 after the formation of the aggregates 10 in the droplets. A plurality of elongated aggregates is formed in each droplet 6. FIG. 6 shows in the same device 60 a plurality of droplets 6 having elongated aggregates. The nature and quantity of droplets 6 have been adjusted so that only one elongated aggregate is present per droplet. The presence of a single aggregate 10 per droplet 6 facilitates measurement. FIG. 7 shows the same chamber 62 after a step of orienting the aggregates along the same detection axis D.

Analysis Method with the Second Apparatus

The analysis method according to the invention of this second apparatus 60 differs from the method previously described in that the measurement is simultaneously performed on the plurality of droplets 6, for example by simultaneously measuring throughout the chamber 62, and not by circulation of the droplets 6 in front of a detector.

One advantage of this method is that it is possible to repeat the measurement of the physical parameter on the same droplet over time, since the droplets are stationary, and thus be able to determine the kinetics of secretion of an element of the secretome.

The method also differs in that it comprises, before the measurement step, a step of orienting the main axis X of the aggregate 10 along a detection axis D.

Advantageously, it will be possible to multiply the detection axes, by applying magnetic fields of variable orientation. This approach has the advantage of making it possible to discriminate the aggregate 10 from other non-magnetic droplet objects, or to reduce parasitic signals. For example, the background fluorescence may be reduced. For example, the detection along different axes makes it possible to distinguish a relocation of the signaling entity 34 to an aggregate of a relocation of the signaling entity 34 on another object of the droplet 6, for example on a cell.

An implementation of this idea consists in applying a magnetic field B1 to align the main axis X of the aggregate 10 in a first orientation D1, then to apply a magnetic field B2 perpendicular to B1 to align the main axis X of the aggregate 10 according to a second orientation D2 that is perpendicular to D1.

Third Apparatus

A third apparatus 70 according to the invention is shown in FIG. 8. This third apparatus 70 differs from the first apparatus 1 in that it further comprises a classification set 72.

In addition, the third apparatus 70 differs from the first apparatus 1 in that the loading set 28 comprises an inlet zone 74 of the inner phase, an inlet zone of the carrier fluid 76, and a junction zone 78. The loading set 28 further comprises an incubation zone 79.

The inlet zone of the internal phase 74 comprises a first inlet duct 80, a second inlet duct 82, and a co-flow duct 84.

The first inlet duct 80 is intended for the introduction of the first mass of fluid 86 that is intended to form part of the inner phase of the droplets. In the example, the first inner fluid mass comprises the particles 12 and a plurality of signaling entities 34.

The second inlet duct 82 is intended for the inlet of the second mass of fluid 88 that is intended to form part of the inner phase of the droplets. In the example, the second inner fluid mass comprises a cell suspension capable of containing tumor cells 90 producing the target element 37.

The concentration of the cells 90 in the second fluid mass is advantageously such that a significant proportion of droplets only contain one cell 90, for example more than 10% of the droplets contains one cell 90.

The co-flow duct 84 allows distribution of the two fluid masses 86, 88 that are intended to form the inner phase.

The inlet zone of the carrier fluid 76 is intended for the inlet of the carrier fluid 8. In the example shown, the carrier fluid 8 enters through two inlet ducts 92.

The junction zone 78 joins the inlet zone carrier fluid 76 and the inlet zone of the inner phase 74. In particular, the junction zone joins the co-flow duct 84 to the inlet ducts 92 of the carrier fluid.

The junction zone 78 is capable of forming the initial droplets 32. The junction zone 78 shown here is a hydrodynamic focusing junction. Examples of hydrodynamic focusing junctions are shown in FIGS. 11 and 12. Alternatively, the initial droplets 32 may be formed in a T junction.

The initial droplets 32 comprising a mixture of the two fluid masses 86, 88 are formed. The initial droplets 32 comprise a dispersion of particles 12 and signaling entities 34.

At least some initial droplets 32 further comprise cells 90, single or in the form of an aggregate of cells.

The incubation zone 79 is located downstream of the junction zone 78. The incubation zone is intended to allow the secretion of the target element 37 by the cells 90, single or in the form of cell aggregates.

Advantageously, the chip comprises means for supplying or exchanging oxygen in the incubation zone 79.

Alternatively, the incubation may be performed outside the device 20.

The third apparatus 70 also differs in that the device 20 further comprises a plurality of classification zones 94, 96 and a means 98 for selectively directing the droplet or portion of the droplet to a classification zone 94, 96.

The classification zones 94, 96 are located downstream of the detection zone 26. The duct 24 comprises a bifurcation 100 with two outlet ducts 102, 104. The first classification zone 94 comprises the first outlet duct 102 that is intended to receive a first group of droplets 106. The second classification zone 96 comprises the second outlet duct 104 that is intended to receive a second group of droplets 108. Alternatively, the device 20 may comprise a larger number of classification zones 94, 96 as a function of the number of sorting criteria.

The means 98 for selectively directing the droplets is, for example, able to direct a droplet 6 to a classification zone 94, 96 by means of a magnetic force.

Alternatively, the droplets 6 are directed by means of electrodes.

For example, the droplets may be directed to a classification zone, by dielectrophoresis, by electrocoalescence with a current, or by surface acoustic waves (SAW).

Analysis Method with the Third Apparatus

The analysis method with the third apparatus 70 according to the invention will now be described.

An apparatus 70, as previously described, is provided. A suspension of magnetic particles 12 and signaling entities 34 is prepared and injected into the first inlet duct 80.

A suspension of cells 90 capable of containing tumor cells is prepared and injected into the second inlet duct 82.

A carrier fluid 8 is supplied and injected into the carrier fluid inlet ducts 92.

The fluids 86, 88 are set in motion by means of the circulation sets 22. The initial droplets 32 are formed in the junction zone 78.

The method further comprises an incubation step in which the cells 90, single or in the form of an aggregate of cells, is capable of secreting, cleaving or releasing the target element 37 of the cell secretome tumor to be analyzed, for example the protein or peptide of the tumor cell secretome. The incubation is thus carried out under conditions and for a time sufficient for the cell 90, in particular when it is in the form of a single cell, to be capable of producing at least one target element 37 of the secretome of a tumor cell.

Typically, the incubation step lasts 5 minutes to 32 hours, for example about 1 to 24 hours, or 2 to 9 hours, in particular for the analysis of cells freshly recovered from a biological fluid of a patient. Alternatively, the incubation step may last 32 to 72 hours, for example about 32 to 48 hours, for example about 36 hours, in particular for the analysis of thawed cells.

Incubation is generally carried out at 37±1° C., with 5% $CO_2$. The incubation is typically carried out in the presence of a buffer or appropriate medium.

One advantage of the method according to the invention is that, compared to the EPISPOT analysis method as described in the patent application EP 1 506 407, the duration of the incubation step may be shortened because of the sensitivity of the method according to the invention. Due to the accumulation of the secretome elements in the small volume of the droplet, with equivalent incubation time, the concentration of the secretome elements to be detected will be higher in the method according to the invention compared to the EPISPOT method. The implementation of the method according to the invention is therefore faster and more sensitive.

The droplets 6 advantageously comprise a culture medium for keeping the cells 90 alive in the droplet for three days or more. It is typically a culture medium for mammalian cells, especially human cells, with or without serum.

The incubation step is carried out in the incubation zone 79 of the device 20.

Alternatively, this step may be performed outside the device 20.

The steps of forming and measuring the aggregate are the same as for the analysis method with the first apparatus 1.

The method differs in that the measurement step is followed by an analysis step. The analysis step makes it possible to determine which group 106, 108 belongs to a droplet 6 according to predetermined criteria, and to generate a droplet classification decision 6 after the measurement step.

According to the classification decision, the droplet 6 is directed towards one of the classification zones 94, 96 by the direction means 98.

In the example shown in FIG. 8, the droplets 106 in which the signal of high fluorescence intensity is located, i.e. mainly in the vicinity of the aggregate 10, are directed into the first classification zone 94. The droplets of the first group 106 correspond, for example, to the third droplets 56 of FIG. 2.

These droplets 106 contain, for example, the tumor cells 90, which are unique or in the form of aggregates of tumor cells, among which the secretome comprises the target element 37. The droplets 106 are optionally recovered so that their contents, and, in particular, the tumor cell(s) contained therein, may be analyzed by other techniques, or so that the tumor cells 90, single or in the form of aggregates of tumor cells, are put back into culture.

The droplets 108 in which a different signal, in particular a substantially homogeneous signal on the droplet 108, was measured are directed to another classification zone 96. The second group of droplets 108 comprises, for example, droplets that do not comprise a cell 90, and droplets containing a single cell 90 that does not produce the target element 37 of the tumor cell secretome in sufficient quantity or quality.

Once the living tumor cells 90 have been identified by their secretome and sorted, numerous subsequent analyses may be performed, possibly after lysis of the droplets and re-encapsulation of the living tumor cells 90 in droplets, such as, for example, analysis of the transcriptome (messenger RNA for gene expression, and microRNA), of the genome, of the epigenome, or of the proteome (Alix-Panabières C, Pantel K. *Clinical Applications of Circulating Tumor Cells and Circulating Tumor DNA as Liquid Biopsy*. Cancer Discov 2016).

Transcriptome analysis, particularly the analysis of mRNA, tumor cells (especially CTCs) may reveal very important information on drug susceptibility and resistance. For example, in metastatic and castration-resistant prostate cancer, the expression of ARV7 mRNA, a truncated form of the androgen receptor that has no binding domain to its ligand but persists in active CTCs could predict the failure of anti-androgen therapies (including therapies using enzalutamide and/or abiraterone). Patients whose CTCs express this ARV7 mRNA may, however, remain taxane-sensitive and detection of this ARV7 splice variant in the CTCs may become a marker for selection of appropriate treatment in these patients.

MicroRNAs (miRNAs) are key regulators of gene expression and have become potential diagnostic markers and targets for anti-cancer therapies. Thanks to an in situ hybridization technique, it is possible to analyze large miRNA (e.g. miR-10b) on the scale of a single cell.

With respect to genome analysis, mutations within genes encode therapeutic targets or signaling proteins downstream of targets that affect the efficacy of targeted therapies. For example, EGFR mutations affect anti-EGFR therapies in lung cancer, and KRAS mutations—a downstream EGFR protein—block the efficacy of anti-EGFR therapies in colon cancer. Recently, analysis of hundreds of CTCs obtained from patients with colorectal cancer has shown strong intra- and inter-patient heterogeneity for the KRAS mutation. CTCs carrying the mutated KRAS genes will escape anti-EGFR therapy, and their early detection may be important in guiding patient choice of treatment.

The cells analyzed in the droplets may be decapsulated from the emulsion. A suitable method for decapsulating the emulsion comprises the addition of 5% v/v 1H, 1H, 2H, 2H-perfluoro-1-octanol (Sigma-Aldrich), followed by incubation for one hour. The phases are separated by centrifugation (for example, 300 g for 5 min), and the cells are collected at the interface of the two phases, aqueous and fluorinated.

To facilitate the collection of cells, the method may comprise the introduction of a third layer, of a density between that of the aqueous phase and that of the fluorinated phase (for example 1.10 g/ml), before centrifugation between the two phases. The third layer is generally an aqueous solution of osmolarity that is suitable for contact with the cells. A suitable solution is, prepared, for example, by dissolving 27.6 g of Nycodenz (Progen) in 100 ml of a solution consisting of 5 mM TrisHCl, 3 mM KCL, 0.3 mM CaNa2EDTA, pH 7.5. The cells are then harvested in the third layer, positioned at the interface of the aqueous phase and the fluorinated phase, thus avoiding taking the fluorinated phase with the cells.

Advantages of the Invention

The use of a dispersion of particles 12 of small size with respect to the size of the droplets ensures a homogeneous distribution of the particles 12 in the droplets 6, and therefore the almost certain formation of a significant size aggregate in each droplet.

Overall, this method makes it possible to assay/quantify an element of the tumor cell secretome, such as a protein or peptide of the tumor cell secretome in the droplet containing the single cell or the aggregate of cells.

The formation of an elongated aggregate 10 provides a better signal-to-noise ratio and a larger dynamic range compared to the test described in Mazutis et al. (Nat prot 2013) where a single bead is encapsulated. In fact the signal generated by the signaling entity 34 will be focused on a width smaller than that of a sphere of equal surface area. The height of the peak as shown in FIG. 2 will therefore be higher than in the case of a single bead for the same number of relocated signaling entities 34.

This method may be used in many biological analysis methods. The method according to the invention may be applied to many types of secretome elements, in particular proteins or peptides of the secretome.

In particular, this invention makes it possible to analyze in a very complete manner the liquid biopsy of the cancer in real time by phenotyping, secretome analysis and molecular analysis of tumor cells, either singly or in the form of aggregates of tumor cells.

The apparatus according to the invention may be integrated as a technological brick in more complex devices, in particular in a high throughput screening device, in a lab on a chip, in a "point of care" device in laboratory instruments, robots, or others.

In addition, the method according to the invention may be integrated into complex protocols for the diagnosis, the discovery of drugs, the discovery of targets, or the evaluation of a drug.

In addition, the microfluidic systems according to the invention and the methods according to the invention may be combined or included in other types of microfluidic components or for other microfluidic functions known in the prior art.

Furthermore, the invention may be particularly useful in combination with various optical methods, including optical detection methods.

The method is applicable, for example, in determining the presence of a target element 37 in the secretome, the concentration of a secreted, salted or cleaved target element 37, thereby establishing characteristics of the tumor cell producing the target element. 37 in the droplet 6.

The method also makes it possible to sort, capture and extract droplets having interesting characteristics, and, in particular, containing a single tumor cell or an aggregate of tumor cells.

In one example, the method comprises the formation of a sandwich, wherein the target element 37 is, on the one hand, linked to the capture element 36 of the particle 12 and, on the other hand, to the signaling entity 34, wherein the signaling entity 34 is fluorescent.

In one example, the capture element 36 is a polyclonal or monoclonal antibody. In one example, the signaling entity 34 is a polyclonal or monoclonal antibody. In one example, the target element 37 is a peptide or a secretome protein.

In one example, the capture element 36 is a nucleic acid, in particular a DNA probe or an aptamer. In one example, the signaling entity 34 is a nucleic acid, in particular a DNA probe. In one example, the target element 37 is a nucleic acid of the secretome, in particular double-stranded DNA, mRNA or miRNA.

In one example, the capture element 36 is a polyclonal or monoclonal antibody or nanobody, or an aptamer directed against a protein present in the membrane or attached to the membrane, or against lipids or sterols. In one example, the signaling entity 34 is a polyclonal or monoclonal antibody. In one example, the target element 37 is an exosome. In another example, several pairs of capture elements 36—target element 37 or capture element triplets 36—target element 37—signaling entity 34 may be analyzed simultaneously, to detect the presence of several target elements 37 of a different nature.

For example, as shown in the droplet in FIG. 13, a droplet may comprise several target elements 37a, 37b of a different nature and several signaling entities 34a, 34b, wherein each is able to form a complex with one of the target elements 37a, 37b. Some particles 12 of the aggregate 10 comprise a capture element 36a intended to capture a first target element 37a, while other particles comprise another capture element 36b intended to capture a second target element 37b.

In some applications, the aggregation of particles 12 is reversible.

In some cases, the presence of the target element 37 renders the aggregation non-reversible and consolidates the aggregate 10 during its formation in the aggregation set 30. The aggregate 10 therefore pre-exists stably only in the droplets 6 containing the target element 37. In the droplets not containing the target element 37, the reversibility of the aggregation of the particles 12 dissolves the aggregate 10 as long as it does not enter the reading zone 26. In a chosen regime of magnetization and fluidics, the aggregate 10 may be formed and orientated only in the presence of this pre-aggregation, which limits the peak acquisition according to FIG. 2 to the droplets containing the target element 37 by another method than via the signaling entity 34.

The present invention finds, in particular, application in the detection and/or characterization of tumor cells isolated from biological fluids. Each cell may release, secrete, or cleave in vitro a number of elements of the tumor cell secretome, in particular a certain number of proteins or peptides, in particular one or more tumor markers for identifying a tumor cell. The present invention also makes it possible to study or characterize the secretome of cells, single or in the form of an aggregate of cells, which will have been identified as tumor cells prior to or simultaneously with their characterization, in particular by the method of detecting tumor cells according to the invention.

The tumor cells are, for example, living circulating tumor cells, hereinafter designated by the abbreviation 'CTCs', isolated from blood, or live disseminated tumor cells, hereinafter designated by the initials 'DTC', isolated from bone marrow, or live tumor cells from any other biological fluid, for example urine or cerebrospinal fluid (CSF).

Aggressive metastatic tumor cells, which are capable of giving distant metastases, are among the cells to which the present invention applies. In particular, aggregated CTCs in the bloodstream could have a much higher metastatic potential than isolated CTCs.

The present invention has the advantage of allowing an analysis of living CTCs, and thus of studying the functionality of these cells, whereas the techniques of the prior art involve the isolation and the fixing of the CTCs before analysis.

The tumor cells may be cancer cells of solid cancer or of liquid cancer (leukemia, lymphoma).

For example, tumor cells may be isolated from biological fluids of patients with solid cancer, for example cancer of the breast, prostate, colon, rectum, thyroid, skin, liver, testis, ovary, etc.

The tumor cells are, in particular, human or animal cells, such as rodent (for example rat or mouse), primate (for example monkey), canine (for example dog) or feline (for example cat).

Advantageously, the cells will have been marked prior to their encapsulation. The cells may in fact be pre-marked, for example with one or more marked antibodies (for example with a fluorochrome) directed against one or more membrane tumor markers, to identify the tumor nature of the encapsulated cell, or of the aggregate of encapsulated cells, by detecting the signal emitted by the marked antibody(ies) at the level of the cell or of the aggregate of cells. This detection may be performed on the circulating droplets as in static mode.

By way of examples, the target element(s) may be cytokeratins such as CK19.

Alternatively, the target element(s) may be tissue markers such as mammaglobin (for breast), prostate-specific antigen (PSA) or human kallikrein 3 (hK3) (for prostate).

Alternatively, the target element(s) may be mesenchymal markers such as "human glandular kallikrein" (hK2), Her2-neu, thyroglobulin, CA19-9, CA15-3 ACE (angiotensin converting enzyme), CA-125, Cathepsin D, alphafoetoprotein, S100 protein, fibroblast growth factor-2 (FGF-2), epithelial growth factor (EGF), etc.

In one example, the single tumor cell 90 is a prostate tumor cell, and at least one target element 37 is PSA (prostate-specific antigen). This marker is specific for prostate cancer. The capture element 36 grafted onto the particles 10 is a first anti-PSA antibody. The signaling element 34 is a second anti-PSA antibody which is marked, in particular, with a fluorochrome such as Alexa 555. This marker is very specific for prostate cancers; its presence alone makes it possible to characterize cells as tumor cells from prostate cancer.

In another example, several markers are detected in combination to characterize the tumor cells. For example, some markers are not specific to one type of cancer, but the combined presence of two different markers makes it possible to identify the type of cancer. The choice of marker combinations suitable for identifying a type of cancer is within the abilities of those skilled in the art.

Thus, the VEGF marker exists in the secretome of many tumor cells. However, its presence with other markers makes it possible to characterize a cancer. Likewise, the presence of the FGF2 marker alone is not sufficient in itself to characterize a cancer.

In the example shown in FIG. 13, it is thus possible to analyze the presence of several types of secret target elements. Each sandwich-type immunoassay detects a distinct target element 37a, 37b secreted by the single tumor cell 90.

The measurement of each fluorescence signal therefore makes it possible to have information on the nature or the phenotype of the cell. Preferably, the signaling entities 36 comprise fluorochromes. A different fluorochrome is preferably associated with each specific binding partner of a different target element, and, in particular, with a different tumor marker.

Thus, in its particularly advantageous embodiments, the method according to the invention allows the detection of CTCs or DTCs by a method of the EPISPOT multiparametric fluorescent type, which uses different pairs of antibodies and different fluorochromes. Examples of fluorochromes include Alexa488 for green, Alexa555 for red, Alexa350 for blue, etc.

The number of target elements 37 that may be analyzed for a single tumor cell is chosen upstream of the experiment by choosing the pairs of functionalized particles with capture elements and signaling entities. For example, it is possible to perform measurements on more than nine different fluorescence channels. This allows, for example, more than nine simultaneous measurements of secretome elements of a single tumor cell to be carried out.

Obtaining Tumor Cells

According to advantageous features of the invention, the detection method comprises a preliminary step of enriching the CTCs or DTCs present in the biological sample.

The enrichment of the cells of the biological sample may be based on the expression of markers expressed on the surface of the cells, the size, the density or the electrical charges of the cells. For example, CTCs may be isolated from blood by leukocyte depletion or by filtration.

The enrichment of the cells of the biological sample may, for example, consist of either a positive sorting of the cells, based on the expression of membrane-specific proteins of the epithelial cells, for example, Epithelial Cell Adhesion Molecule (EpCAM), or on sorting negative cells based on the expression of specific markers on the surface of unwanted hematopoietic cells, as exemplified by CD45, CD4, CD8, CD19, CD56.

The cells may be sorted according to their size through the use of a membrane-filter which will retain the large cells and let the hematopoietic cells of smaller size pass. The cells may be sorted according to their density by centrifugations on specific gradients.

The cells may be sorted according to their electrical charge by dielectrophoresis because the CTCs/DTCs have a charge that is different from those of the hematopoietic cells, by the use of dielectrophoresis.

Any other enrichment method for obtaining viable cells known to those skilled in the art is suitable for the purposes of the invention. It will therefore be a method that does not implement fixing or permeabilization of CTCs/DTCs in order to maintain their functionality (Alix-Panabières and Pantel, Expert Rev Mol Diagn 2015; 15(11): 1411-7).

The cells obtained after the enrichment step may also be identified as being tumorous in the droplets. According to one embodiment, the enriched cells are marked with a marked antibody (in particular by fluorescence) directed against one or more tumor cell surface markers. The tumor cells then become marked, in particular by fluorescence, with their membrane. By way of example, the cells may be marked with (1) an anti-EpCAM fluorescent antibody and/or an anti-E-cadherin fluorescent antibody to detect the expression of EpCAM and/or E-Cadherin on the cell surface in order to identify any epithelial cell, and/or (2) a fluorescent anti-PSMA antibody (prostate-specific membrane antigen) to identify tumor cells of the prostate, and/or (3) an anti-fluorescent anti-N-Cadherin to identify mesenchymal cells that have undergone an epithelial-mesenchymal transition (EMT), and/or (4) an anti-plastin 3 antibody that targets a new marker, plastin 3, which is not under-expressed during EMT, and which allows the detection of epithelial and mesenchymal tumor cells, This step precedes the encapsulation of the cells of the sample and makes it possible to determine the phenotype of the CTCs or DTCs.

The present invention is particularly advantageous because the number of droplets is, in theory, not limited and may reach in practice, for example, up to 100,000 and even up to 1,000,000 droplets. It is thus possible to have droplets not comprising cells or non-enriched cells. If the encapsulated cell is not tumorous, the signal will be different and the droplet may be discarded. The system thus makes it possible to refine the purification. It is therefore suitable for working from biological samples that are not rich in CTCs.

This is particularly advantageous for detecting rare tumor cells in the blood, such as CTCs.

EXAMPLES

Examples of the implementation of the method will now be described.

The protocol of the following examples includes:
- the preparation of several aqueous solutions, containing the particles 12, the signaling entity 34 and the target element, or a cell capable of secreting it, releasing it or cleaving it in the droplet,
- the injection of the aqueous solutions at the inlet of a droplet generation chip,
- the generation of droplets comprising all the reagents of the test
- the incubation of the solution containing the droplets,
- the injection of the droplets into an apparatus according to the invention (Examples 1 and 2 respectively correspond to the first apparatus 1 or to the second apparatus 60),
- the measurement of the results of the test
- optionally, sorting droplets according to the measurement.

Example 1: Device for Generating Droplets and Measuring Type 1 Droplets

The production of droplets, otherwise known as compartmentalization, is performed after mixing a reagent solution and an on-chip sample solution.

Solutions are kept on ice until compartmentalization to prevent degradation of reagents and samples.

The reagent solution is sucked into a reservoir connected to a 1 mL Hamilton syringe filled with mineral oil (Sigma Aldrich, #330760) just prior to starting compartmentalization. The samples to be screened are mixed with the working solution just before compartmentalization and then transferred to a glass vial previously filled with fluorinated oil (3M, NOVEC HFE-7500) and the vial is kept at 4° C. on ice.

Capillaries, advantageously made of PTFE with an internal diameter of 0.3 mm (sold by Fischer, #11919445), make it possible to connect the vial and the reservoir of the reagent solution to the device for forming droplets.

These two solutions are injected onto a droplet formation chip which makes it possible to generate droplets comprising an equal volume of each of the two solutions.

The volume of the droplets is chosen by the user from the flow rate of the fluorinated oil. Advantageously, the volume of the droplets is 33 picoliters. The fluorinated oil is the carrier fluid 8. It constitutes the continuous phase of the emulsion comprising the droplets.

Solutions of test reagents and samples to be screened are injected into the chip at the same rate, advantageously at 200 microliters/hour for each solution. The flow rate is imposed by a standard syringe pump system, for example a Cetoni neMESYS pump or by a pump controlling the pressure, for example the system marketed by Fluigent.

The droplets are generated at a hydrodynamic focusing junction as shown in FIGS. 11 and 12. The external phase is here a fluorinated oil (3M, NOVEC HFE-7500) to which two % w/v of surfactants have been added (for example, a triblock copolymer comprising two perfluoropolyether tails (PFPE) (molecular weight approximately ~6,000 g/mol) and a PEG head (~600 gmol).

FIG. 11 and FIG. 12 show flow-focusing devices for mixing a flow containing the magnetic beads mixed with the other reagents and a flow containing the samples before the formation of droplets at the hydrodynamic focusing junction on the right. In FIG. 11, the magnetic particles measure 500 nm in diameter, while in FIG. 12 the magnetic particles measure 200 nm in diameter.

A second step is the collection stage. A vial held at 4° C. under the magnetic field, advantageously generated by a ring magnet (Amazing magnet H250H-DM), allows the collection of droplets. A short capillary makes it possible to connect the flask to the chip. Ideally, the outlet capillary measures less than 20 cm, preferably 10 cm.

The droplets are advantageously incubated at 37° C. for 20 to 90 minutes and under magnetic fields, wherein the incubation time and temperature depend on the analysis carried out and on the type of production entity 90 and target element 37 studied.

Following the incubation, the vial containing the emulsion is transferred at 4° C. and is still kept in a magnetic field.

The first type of device is a device according to the invention as described in FIG. 1.

The vial containing the droplets is connected to a chip for reinjection, wherein, on the one hand, the vial is connected to the chip and, on the other hand, to a pressure system, a pressure pump or a syringe, wherein and its pump constitutes the circulation set 22.

The spacing set 31 comprises two oil inlets connected to the chip. These inlets are intended to inject oil, preferably fluorinated oil, for spacing the droplets of the emulsion as shown in FIG. 9.

The flow rates of the spacing oil are advantageously each fixed at 300 microliters/hour, and the flow rate of the circulation set is advantageously set at 50 microliters/hour to make it possible to adjust the flow rate and the reinjection frequency of droplets in order to obtain a frequency of between 250 and 1000 Hz.

A pair of permanent magnets 38, preferably provided by K&J Magnetics, # BC 14-N52, is placed on either side of the chip around the main channel 24. These magnets 38 are intended to generate and guide the aggregates of beads during the reinjection of the droplets.

Software for the control of equipment, for example lasers or photomultipliers, is created to analyze and sort the droplets. The sorting system requires an FPGA card to perform real-time signal analysis.

The measurement is made in the droplets one by one after their passage in the spacing set and these droplets may be sorted to a desired outlet after the reading zone shown in FIG. 10.

When sorting and recovery are desired, the sorted droplets and unsorted emulsions are collected on ice and the droplet content is recovered from standard protocols.

Example 2: Device for Measuring Type 2 Droplets (Second Device 60)

The second type of measuring device is a droplet storage chamber produced in a 2-dimensional plane. This example presents two possible alternatives for making such chambers.

The first is a chamber manufactured by conventional PDMS microfabrication, preferably comprising pillars positioned in a regular manner to prevent the collapse of the chamber as illustrated in FIGS. 4 to 7.

The second is a glass chamber according to the invention PCT/FR2009/051396. Advantageously, this approach makes it possible to incubate the droplets for long periods (>1H) without moving the droplets. The droplets may therefore be collected directly in such a chamber after their formation.

In one example, the measuring device is a two-dimensional reading device, for example in a glass chamber. The magnetic field is generated by a pair of permanent magnets 38 preferably provided by K&J Magnetics, #BY042, placed on either side of the storage chamber. These magnets 38 are intended to generate and guide the aggregates of beads in the droplets stored in the chamber.

The fluorescent signal of the signaling entity 34 relocated to the magnetic bead line is measured by epifluorescence microscopy.

Example 3: Quantification of a Tumor Marker in a Type 1 Measuring Device

The purpose of this example is to demonstrate the quantification of a tumor marker.

In this example, the target element 37 is a tumor marker and, more particularly, a vascular epithelial growth factor (VEGF) angiogenesis marker which is already contained in the solution to be screened, this example does not implement cells.

The droplets measure 33 picoliters in this example.

The preparation of the droplets comprises:
the preparation of two aqueous solutions, called "reagent solution" containing the particles 12, the signaling entity 34 and the "sample solution to be screened" containing the target element in the examples below,
the injection of the two aqueous solutions at the inlet of the droplet generation chip,
the generation of droplets comprising an equal volume of each of the two solutions,
the measurement of the droplets in a type 1 device.

The reagent solution contains:
particles 12 which are colloidal magnetic particles here, such as particles conjugated with steptavidin (for example, Ademtech streptavidin plus particles), which are functionalized with a capture element 36, for example a VEGF-specific antibody conjugated with biotin (for example the antibody Ref 500-P10GBt, Peprotech). Other methods of immobilization are possible and are known to those skilled in the art, such as the use of carboxyl and 1-ethyl-3-[3-(dimethylamino)propyl]carbodiimide (EDC) particles, for example,
a signaling entity 34 which is here an antibody against VEGF functionalized with a fluorescent molecule, such as bevacizumab (supplied by Montpellier University Hospital) which is functionalized with an N-Hydroxysuccinimide (NHS ester) of Alexa Fluor 647 or the like. Other combinations of fluorophores or functionalization methods are possible; and
a dye for the detection of droplets 6, for example sulforhodamine B.

These reagents are diluted in a solution called a "working solution". The working solution comprises:
RPMI 1640 (Eurobio, Ref CM1RPM00-01),
L-Glutamine 200 mM/100× (Eurobio, Ref CSTGLU00): 1% final,
Insulin-Transferin-Selenium (ITS) 100× (GIBCO, Ref 51300-044): 1% final,
fetal calf serum decomplemented 10% (Eurobio, Ref CVFSVF00-01), EGF Human (Epidermal Growth Factor)—Miltenyi (Ref 130093564): 20 ng/mL final,
bFGF (Basic Fibroblast Growth Factor)—Miltneyi (Ref 130097750): 10 ng/mL final,
antibiotics (Penicillin G at 10,000 IU/500 mL+Gentamicin at 1 mg/500 mL),
25 mM of HEPES buffer at pH 7.4,
0.1% v/v Pluronic F-68 supplied by Life Technologies.

The magnetic colloidal particles 12 are treated before use. The particles 12 are provided by Chemicell (ScreenMAG) or Ademtech (Bio Adembeads) in a storage solution. Advantageously, streptavidin (or the like) is already immobilized on the particles by the suppliers (such as Ademtech streptavidin plus beads). They are retained on a magnetic medium in order to remove the storage solution and then they are suspended in an excess of pluronic F-127 at 10% w/w (ThermoFisher), advantageously 10× the initial volume of particles, and incubated for fifteen minutes in an ultrasonic bath at 4° C.

After this treatment, the magnetic colloidal particles 12 are washed twice in PBS and suspended in the working solution. In this solution, the biotinylated version of the capture molecule is added in excess for 1 hour (room temperature).

Advantageously, the particles 12 are washed twice and suspended in the working solution.

Fluorescent reagents are centrifuged for five minutes at least at 12,000 g and at 4° C. before use to remove traces of aggregates of reagent.

The sample solution to be screened comprises:
a target element 37, here VEGF, capable of being captured by the capture element 36; and
the working solution.

The sample solution to be screened contains different concentrations of the target element 37 (VEGF) (provided, for example, by Genscript) diluted in the working solution (see above).

The concentrations of target element 37 (VEGF) in the sample solution to be screened are 0 nM, 5 nM, 20 nM or 50 nM.

The reagent solution contains the following reagents:
0.16% w/v of magnetic particles functionalized with a capture element 36, here a VEGF-specific antibody as described above,
50 nM of the appropriate signaling entity 34, here another specific VEGF antibody conjugated with a fluorescent molecule,
1 µM of sulforhodamine B (for the marking of droplets).

This solution is completed by the working solution (see above).

This makes it possible to obtain four different emulsions with, respectively, 0 nM, 2.5 nM, 10 nM or 25 nM of target element 37 (VEGF).

The droplets are then analyzed by means of a type 1 device measuring the fluorescence of the fluorophore of the signaling entity 34, such as Alexafluor488 or 647.

Example 4: Quantification of Two Tumor Markers Simultaneously in a Type 1 Measuring Device The object of this example is to demonstrate the quantification of two signaling entities (two tumor markers) simultaneously. This example is similar in every respect to Example 3 with the difference that two distinct target elements 37 are measured simultaneously. The two target entities are tumor markers, VEGF and CK19 [Cytokeratin 19].

The reagent solution contains:
particles 12 which are here colloidal magnetic particles, functionalized with two capture elements 36, here specific VEGF antibodies (Ref 500-P10GBt, Peprotech) and specific CK19 antibodies (Progen KS19.2) which are immobilized on the particles by an appropriate method, such as the biotin-streptavidin pair, a first signaling entity 34 which is here a specific VEGF antibody fluorescently marked with a suitable fluorophore, such as a conjugation of bevacizumab with AlexaFluor647, a second signaling entity 34 which is here a specific CK19 antibody, such as (Progen KS19.1), fluorescently marked by the fluorophore Alexa Fluor 488, a dye allowing the detection of droplets 6, such as sulforhodamine B.

These reagents are diluted in a solution called the working solution that is identical to that used in Example 2.

The sample solution to be screened comprises:

a first target element 37, here VEGF, capable of being captured by the first capture element 36, a second target element 37, here CK19, intended to be captured by the second capture element 36, the working solution.

The sample solution to be screened contains different concentrations of the first target element 37 (VEGF), for example provided by Genscript, while the second target element 37 (CK19), for example provided by MyBioSource) dilutes the working solution (see above).

The concentrations of the first target element 37 (VEGF) in the sample solution to be screened are as follows: 0 nM, 2.5 nM, 10 nM or 25 nM. The concentrations of the second target element 37 (CK19) in the sample solution to be screened are 0 nM, 2.5 nM, 10 nM or 25 nM. A total of 16 concentration combinations of the two target elements are prepared.

The droplets are analyzed by means of a type 1 device simultaneously measuring the fluorescence of the fluorophores, such as AlexaFluor488 and 647, on the two signaling entities 34.

Example 5: Quantification of Secreted Tumor Marker on the Scale of a Single Cell in a Type 1 Measuring Device The purpose of this example is to demonstrate the possibility of detecting and quantifying a tumor marker secreted at the single cell level. This example is similar in all respects to Example 3 except that the target element 37 (VEGF) is secreted by a producing entity 90 (a cell) in the droplet during an incubation phase. The cells are either a colon cancer CTC line (CTC-MCC-41.4 obtained in the LCCRH laboratory), or a cell population of CTC-enriched colon cancer patients. In the second case, CTCs are enriched with the RosetteSep protocol (StemCell Technology procedure) via leukocyte depletion.

The enrichment protocol for CTCs using the RosetteSep technique is as follows:

Transfer the blood (15 mL) from the EDTA tube into a 50 mL falcon;

Add 20 µl of Rosette StemCell (Human Circulating Epithelial Tumor Cell Enrichment—Ref 15167) per mL of whole blood;

Mix and turn slowly on the MACS mix for at least 20 minutes;

Place the appropriate volume of Ficoll (Lymphocyte Separation Medium) in a falcon, according to the volume of blood as recommended by the supplier;

Dilute the blood with ½ PBS 1×/2% SVF;

Deposit the solution [blood+rosettes+PBS] gently on the surface of the Ficoll and centrifuge for 20 min at 1200 g without brake.

Recover all the upper part of the Ficoll with the cellular ring (where the circulating tumor cells are to be found); Wash 2× with PBS/SVF 2% qs 50 ml.

The cell pellet obtained contains the circulating tumor cells and is ready to be used for the single-cell EPISPOT according to the invention.

The sample solution to be screened contains cells suspended in the working solution described in Example 3. Advantageously, the concentration of cells per droplet is 0.3 cells per droplet. An emulsion with droplets of 33 picoliters, as here, contains more than $30.10^6$ droplets per milliliter. To have 0.3 cells per drop, it takes about $18.10^6$ cells per milliliter in the sample solution to be screened (which is concentrated twice in relation to the droplets). It should be noted that the cell concentration in the sample solution to be screened is twice as large as the final concentration since the two aqueous solutions will be mixed in a droplet with a 50/50 ratio.

Example 6: Quantification of Two Tumor Markers Simultaneously Secreted at the Scale of a Single Cell in a Type 1 Measuring Device The object of this example is to demonstrate the possibility of simultaneously detecting and quantifying two tumor markers secreted at the single cell level. This example is similar in every respect to Example 5 with the difference that two distinct target elements 37 are measured simultaneously. The two target elements are the tumor markers VEGF and CK19, which are measured as in Example 4.

Example 7: Sorting of Cells According to a Secreted Tumor Marker

The purpose of this experiment is to demonstrate the screening of cells according to a secreted tumor marker. This example is similar in every respect to Example 5 except that the droplets with a large fluorescence signal corresponding to the fluorescence of the fluorophore on the signaling entity 34 are sorted by "fluorescence activated dielectrophoresis" (FADS) as described in Baret et al. (Lab Chip 2009, 9, 1850-1858). The sorted and collected droplets are broken and the cells are recovered as described in Mazutis et al. (Nat Prot 2013, 8, 870-891).

Example 8: Sorting of Cells According to Two Secreted Tumor Markers

The object of this experiment is to demonstrate the screening of cells according to two secreted tumor markers. This example is similar in all respects to Example 7 with the difference that two distinct target elements 37 are measured simultaneously. The two target elements 37 are the tumor markers VEGF and CK19, which are measured as in Example 4. The droplets with a large fluorescence signal corresponding to the fluorescence of the fluorophore such as Alexafluor488 on the first signaling entity 34, and Alexafluor647 on the second signaling entity 34 is sorted by "fluorescence activated dielectrophoresis" (FADS) as described in Baret et al. (Lab Chip 2009, 9, 1850-1858). The sorted and collected droplets are broken and the cells are recovered as described in Mazutis et al. (Nat Prot 2013).

Example 9: Quantification of a Tumor Marker in a Type 2 Measuring Device (Second Apparatus 60)

The object of this example is to demonstrate the quantification of a tumor marker in a type 2 device, i.e. a chamber in which the droplets are distributed in two dimensions in a single layer. This example is similar in every respect to Example 3 with the difference that the droplets measure 40 picoliters and are analyzed in a type 2 measuring device. A 38 µm high chamber is created between two glass slides. An inlet and an outlet are made in the upper glass slide and respectively provided with a standard connector for connecting the connection capillaries.

Example 10: Quantification of Two Tumor Markers Simultaneously in a Type 2 Measuring Device (Second Apparatus 60)

The object of this example is to demonstrate the quantification of two signaling entities (two tumor markers) simultaneously in a type 2 device. This example is similar in every respect to Example 4 except that the droplets measure 40 picoliters and are analyzed in a type 2 measuring device, as in Example 9.

Example 11: Kinetic and Quantitative Measurement of a Secreted Tumor Marker on the Scale of a Single Cell in a Type 2 Meter (Second Apparatus 60)

The purpose of this example is to demonstrate the kinetic and quantitative measurement of a secreted tumor marker at the scale of a single cell in a type 2 device. This example is similar in every respect to Example 5 except that the droplets measure 40 picoliters and are analyzed in a type 2 measuring device, as in Example 9. By measuring the evolution, at the scale of a single cell, of the fluorescent signal of the relocated signaling entity 34 on the magnetic bead line the secretion rate of the target element 37 (the VEGF tumor marker) may be determined.

Example 12: Kinetic and Quantitative Measurement of Two Tumor Markers Simultaneously Secreted at the Scale of a Single Cell in a Type 2 Measuring Device (Second Apparatus 60)

The object of this example is to demonstrate the simultaneous kinetic and quantitative measurement of two secreted tumor markers at the scale of a single cell in a type 2 device. This example is similar in all respects to Example 6 except that the droplets measure 40 picoliters and are analyzed in a type 2 measuring device, as in Example 9 except that two distinct target elements 37 are measured simultaneously. The two target entities are the tumor markers VEGF and CK19, which are detected as in Example 10.

By measuring the evolution, at the level of the single cell, the fluorescent signals of the two signaling entities 34 relocated on the magnetic bead line, the secretion rate of the two target elements 37 (the VEGF and CK19 tumor markers) may be determined.

Implementation Examples

FIG. 14 illustrates the quantification of a tumor marker in a type 1 device. The graph shows the peak intensity value obtained for the channel measuring the green fluorescence. The droplets comprise beads coated with a biotinylated anti-PSA antibody. The beads are aligned to form a column. With 25 nM PSA, the fluorescence of the secondary anti-PSA antibody is relocated to the magnetic bead column, which increases the intensity peak value (n=200,000). The error bar shows the standard deviation. The same measurement is made for droplets containing LnCAP cells which have been incubated for 1 hour at 37° C. in the droplets. LnCAPs are cells derived from an epithelial cell line derived from human prostate carcinoma.

FIG. 15 shows the sorting of droplets in a type 1 device. This graph shows the possibility of measuring PSA-secreting cells in a type 1 device. Three different droplet populations may be distinguished because of their different droplet codes. (represented along the abscissa axis, corresponding to the fluorescence of the marker Sulforhodamine B). From left to right, we observe the emulsion of cells to be sorted, i.e. the positive control and the negative control. In the fluorescence channel shown on the ordinate axis, the relocation of the anti-PSA on the column of beads is illustrated. The droplets included in the black rectangle are positive droplets for the secretion of PSA and containing a cell.

FIG. 16 shows a sorting of droplets in a Type 1 device. This graph shows a selection window for EpCAM-positive droplet sorting from a droplet emulsion containing cells. The loading is about 5%. This shows a good correlation between EpCAM positivity in the selection window and the cell loading. The ordinate axis represents the maximum value measured within the droplet (i.e. the peak corresponding to the cell). The x-axis represents the integral of the signal under the peak.

FIG. 17-20 illustrate sorting based on two criteria in a type 1 device. FIG. 17 shows a "gate 5" selection window for sorting EpCAM positive cells. FIG. 18 shows a "gate 6" selection window for PSA secreting cells. To be selected, the two criteria must be satisfied, i.e. the selected droplets correspond to the droplets with measurements in the "gate 5" and "gate 6" windows.

The images of FIGS. 19 and 20 represent droplets successfully sorted according to two criteria: the secretion of PSA (FIG. 19), and the expression of EpCAM. (FIG. 20). Empty droplets (negative control) have also been sorted to facilitate the transfer of the droplets of interest into the display chamber. Starting from an emulsion with 0.2% droplets of interest, a 20% enrichment of droplets of interest is obtained. By counting the negative control droplets preserved for the transfer of the droplets, an effective droplet transfer is obtained at approximately 99%.

FIGS. 21 to 23 illustrate quantification of a tumor marker in a type 2 device. FIG. 21 (in the bright field) and 22 (in a fluorescence channel) show the secretion of PSA by LNCAP cells. These cells are incubated for one hour in the droplets and the secretion of PSA results in the relocation of the fluorescence on the columnar particle aggregate.

FIG. 23 illustrates a calibration curve for the quantification of PSA obtained from the droplet table. The curve has a shape generally observed for non-washing immunoassay experiments. After an abrupt increase phase (up to 60 nM) in which the protein binds to the beads, there is a decrease in the fluorescence relocation due to saturation on the beads and an increase in free PSA concentration. The data are presented as an average and error type of the average (SEM).

This calibration curve was made from the soluble form of the PSA protein at different concentrations with two respective antibodies. The concentrations of the reagents, beads and detection agents are adjusted so that the PSA capacity is about 70 nM. The system is very sensitive to the lowest concentrations below 70 nM. It was determined that the white limit (corresponding to the strongest signal expected in an empty drop) is 1.047. This value must be compared to the average value of 1.031 obtained for a concentration of 0 nM. The detection limit, i.e. the smallest distinguishable amount of background, is 2.5 nM PSA, corresponding to only 60,000 molecules. By incubating cells for one hour, all the cells that secrete more than 16 molecules per second may be detected. By prolonging the incubation time to 2 hours, this limit may be reduced to cells secreting 8 molecules per second, etc. The secretion rates reported in the literature for other molecules may vary between 10 and 10,000 molecules per second depending on the cell type and the secreted fraction. This shows that the order of magnitude obtained is satisfactory.

In addition, the calibration curve shows a signal increase at higher concentrations. For example at about 500 nM of PSA, the signal may be significantly distinguished from the background noise. This is advantageous for experimental developments since even cells with a very high secretion level may be detected.

FIGS. 24 and 25 illustrate quantification of a tumor marker in a type 2 device. FIG. 24 (in the bright field) and 25 (in a fluorescence channel) represent the secretion of protein CK19 by a SK-BR-3 cell. SK-BR-3 is a cell line derived from a tumor of human breast cancer.

CK19 is usually a protein integrated into the cell membrane. However, it may be detached and relocated to the elongated aggregate.

An epithelial cell line derived from human prostate carcinoma (LnCAP) is used for experiments to observe cell secretion of PSA.

We found that temperature is an important factor since protein secretion could only be observed around physiological temperatures and not at lower temperatures such as 25° C. At lower temperatures, the signals relocated to the cells and not to the particles, showing that the PSA was bound to the membrane or that a similar phenomenon was occurring.

The cell of the LnCAP line was further used to determine the percentage of PSA secretion of these cells. Considering the literature and previous experiences, we know that not all cells will produce PSA continuously. The idea behind this experiment is to collect the percentage of cells that secrete PSA within the LnCAP population. This experiment is performed at 37° C. and the secretion signals are measured at 0, 30 and 60 minutes.

The following table represents the conditions and results of the PSA secretion experiment using LnCAP cells as a model.

| Incubation time at 37° C. (min) | 0 | 30 | 60 |
|---|---|---|---|
| Number of droplets | 5860 | 6352 | 5745 |
| Number of cells | 53 | 57 | 52 |
| Fluorescence relocation on the elongated aggregate | 0 | 16 | 27 |
| Fluorescence relocation on the cells | 19 | 11 | 6 |
| No relocation found | 34 | 30 | 19 |
| % of cells secreting the marker | 0 | 27.9 | 52.25 |
| % of antibodies relocated to cells | 36 | 19.2 | 11.6 |

At 0 minutes, no fluorescence relocation is found at the level of the extended aggregate. However, it was noticed that the detection agent was relocated on the membrane of some cells. This phenomenon is probably related to culture conditions and centrifugation at room temperature. We made the same observation for measurements at 30 minutes or 60 minutes, but the number of cells with the detection agent relocated on the membrane decreased steadily while the percentage of cells secreting the marker increased.

Accordingly, we may analyze the secretion pattern of individually encapsulated LnCAP cells.

FIG. 26 illustrates the measurement of the kinetics of a secreted marker in a Type 2 device. FIG. 26 shows a PSA secretion pattern for individual LnCAP cells encapsulated in droplets for one hour and then measured at ten minute intervals.

Here, it is shown that the secretion rate of individual cells is varied, although similar distributions have been found for other cell lines. We also show that secretion follows sudden kinetics rather than regular release.

It was observed that some cells secrete more than 800 PSA molecules while the majority of cells secrete very few PSA molecules (about 10 molecules per cell) or none at all (these cells have not been shown.

To simulate the detection of circulating tumor cells (CTCs) in the blood, LnCAP cells were mixed with Jurkat cells. Jurkat cells come from an immortalized line of human Lymphocite T. Both cell lines were cultured in RPMI medium with 10% FBS and encapsulated in droplets. These experiments show that it is in fact possible to detect small quantities of cells. We performed the experiment for different concentrations of LnCAP in Jurkat cells. The size of the cell with a fluorescence marker was used for detection.

The following table shows in the results of the experiment.

| Dilution Rate of LnCAP in Jurkat | Tested (corresponding to the dilution ratio found) | Number of LnCAP expected | Number of LNCAP found | Total number of cells |
|---|---|---|---|---|
| 0.0001 | 0.0001 | 3 | 4 | 30284 |
| 0.001 | 0.001 | 31 | 32 | 31612 |
| 0.001 | 0.0004 | 8 | 4 | 8184 |
| 0.001 | 0.001 | 2 | 2 | 1701 |
| 0.01 | 0.0093 | 45 | 42 | 4498 |
| 0.1 | 0.07 | 198 | 138 | 1975 |

The preliminary study shows that the minimum detection of LnCAP may be 0.0001.

This experiment was constructed to detect PSA in droplets and show that LnCAP cells secrete PSA at a detectable level. The experiments show detection sensitivity in cells artificially mixed with other cells.

The invention claimed is:
1. A method for detecting and/or characterizing a live tumor cell isolated from a biological fluid of a patient with cancer, comprising:
   supplying a plurality of droplets contained in a carrier fluid and dispensed into a microfluidic chamber of an apparatus, at least one of the plurality of droplets containing at least one aggregate of magnetic or paramagnetic particles defining an elongated object along a main axis under a magnetic field, wherein the magnetic or paramagnetic particles are functionalized with a capture element adapted to fix a target element, wherein each droplet in said plurality of droplets comprises a fluorescent, radioactive, or colored signaling entity that is capable of detectably fixing the target element, and wherein at least a portion of said plurality of droplets contain the live tumor cell and are capable of producing at least one target element of a secretome of the live tumor cell capable of being fixed on the aggregate of magnetic or paramagnetic particles functionalized with the capture element;

measuring at least one physical parameter selected from the group consisting of radioactivity, colorimetry, and fluorescence that is characteristic of the fixing of a target element of the secretome of the live tumor cell on the aggregate of particles; and detecting and/or characterizing the live tumor cell from the measurement of the at least one physical parameter that is characteristic of the fixed target element on the aggregate of particles;

wherein the live tumor cell is selected from the group consisting of a circulating tumor cell (CTC) and a disseminated tumor cell (DTC).

2. The method according to claim 1, wherein the method is a method for detecting and/or characterizing a single live tumor cell comprising:

supplying a plurality of droplets contained in a carrier fluid, at least one of the droplets comprising at least one aggregate of particles defining an elongated object along a main axis, said at least one of the droplets containing the single live tumor cell;

incubating the at least one of the droplets (containing a single live tumor cell under conditions and for a time sufficient for the single live tumor cell to become capable of producing at least one target element of the secretome of the single live tumor cell that is capable of being fixed to the aggregate of particles;

measuring at least one physical parameter selected from the group consisting of radioactivity, colorimetry, and fluorescence, each physical parameter being characteristic of the fixing of a distinct target element from the secretome of a tumor cell on the aggregate of particles; and detecting and/or characterizing the single live tumor cell from the measurement of the at least one physical parameter.

3. The method according to claim 1, wherein the method further comprises measuring at least one physical parameter locally at a plurality of points in the plurality of droplets and determining the integral of the measured values within the plurality of droplets.

4. The method according to claim 1, wherein measuring at least one physical parameter is performed in a microfluidic chamber without circulation of the plurality of droplets.

5. The method according to claim 1 further comprising:

providing a device comprising a set for putting in circulation the plurality of droplets and a plurality of classification zones, and a drop director for selectively directing the plurality of droplets or a portion of the plurality of droplets towards a classification zone, classifying the plurality of droplets or a portion of the plurality of droplets, and selectively choosing one of the plurality of classification zones, transporting the plurality of droplets or a portion of the plurality of droplets, to the chosen classification zone.

6. The method according to claim 1, wherein at least one droplet comprises at least two distinct signaling entities, wherein each of the at least two signaling entities is capable of detectably forming a complex with a distinct target element on the aggregate of particles, wherein the method further comprises measuring a signal indicating the concentration of each relocated signaling entity.

7. The method according to claim 6, wherein at least a portion of the droplets comprise the live tumor cell wherein said live tumor cell is capable of secreting, cleaving or releasing one or more elements of a secretome of the live tumor cell, wherein each element of the live tumor cell secretome is a distinct target element, and wherein the measurement of the signal indicates the concentration of each of the relocated signaling entities and allows quantification of the distinct target element of the live tumor cell secretome.

8. The method according to claim 1, wherein the live tumor cell is isolated from a patient with a solid cancer selected from the group consisting of cancers of the breast, prostate, colon, rectum, thyroid, skin, liver, testis, and ovary.

9. The method according to claim 1, wherein the target element of the secretome of the tumor cell capable of being fixed on the aggregate of particles is a specific marker of the secretome of a live tumor cell.

* * * * *